(12) United States Patent
Minami

(10) Patent No.: US 10,450,344 B2
(45) Date of Patent: Oct. 22, 2019

(54) ANTIBODY-BINDING POLYPEPTIDE, ANTIBODY-BINDING FUSION POLYPEPTIDE, AND ADSORPTION MATERIAL

(71) Applicant: FUJIFILM Corporation, Tokyo (JP)

(72) Inventor: Koichi Minami, Kanagawa (JP)

(73) Assignee: FUJIFILM Corporation, Minato-Ku, Tokyo (JP)

(*) Notice: Subject to any disclaimer, the term of this patent is extended or adjusted under 35 U.S.C. 154(b) by 19 days.

(21) Appl. No.: 15/469,660

(22) Filed: Mar. 27, 2017

(65) Prior Publication Data

US 2017/0210777 A1 Jul. 27, 2017

Related U.S. Application Data

(63) Continuation of application No. PCT/JP2015/075157, filed on Sep. 4, 2015.

(30) Foreign Application Priority Data

Sep. 29, 2014 (JP) .................... 2014-199131
Mar. 31, 2015 (JP) .................... 2015-073147

(51) Int. Cl.
*C07K 1/22* (2006.01)
*C07K 7/06* (2006.01)
*C07K 7/08* (2006.01)
*C07K 14/00* (2006.01)
*C07K 17/00* (2006.01)

(52) U.S. Cl.
CPC ............... *C07K 1/22* (2013.01); *C07K 7/06* (2013.01); *C07K 7/08* (2013.01); *C07K 14/00* (2013.01); *C07K 14/001* (2013.01); *C07K 17/00* (2013.01); *C07K 2319/00* (2013.01)

(58) Field of Classification Search
CPC .................... C07K 7/08; C07K 1/22
See application file for complete search history.

(56) References Cited

U.S. PATENT DOCUMENTS

| 4,816,441 | A | 3/1989 | Zeuthen et al. |
| 5,084,398 | A | 1/1992 | Huston et al. |
| 6,743,894 | B1* | 6/2004 | Chen ............. A61K 38/30 530/317 |
| 7,993,650 | B2* | 8/2011 | Carlsson ............. C07K 14/31 424/184.1 |
| 2007/0178541 | A1* | 8/2007 | Pedersen ............. G01N 33/564 435/7.32 |
| 2011/0144302 | A1 | 6/2011 | Jarstad et al. |
| 2012/0264156 | A1 | 10/2012 | Beaulieu et al. |
| 2014/0100356 | A1 | 4/2014 | Yoshida et al. |

FOREIGN PATENT DOCUMENTS

| EP | 0223579 A2 * | 5/1987 | ............ C07K 14/31 |
| EP | 2208787 A1 * | 7/2010 | ............ C07K 14/31 |
| JP | 62-126199 A | 6/1987 | |
| JP | 2-501985 A | 7/1990 | |
| JP | 2011-521653 A | 7/2011 | |
| RU | 2012 119 798 A | 11/2013 | |
| WO | 97/37677 A1 | 10/1997 | |
| WO | WO-2009146755 A1 * | 12/2009 | ............ C07K 14/31 |
| WO | 2011/133894 A2 | 10/2011 | |
| WO | 2012/133342 A1 | 10/2012 | |

OTHER PUBLICATIONS

Mero (Covalent Conjugation of Poly(Ethylene Glycol) to Proteins and Peptides: Strategies and Methods, Bioconjugation Protocols: Strategies and Methods, Methods in Molecular Biology, vol. 751, Chapter 8, 2011). (Year: 2011).*
Chen (Fusion Protein Linkers: Property, Design and Functionality, Adv Drug Deliv Rev. Oct. 15, 2013 65: 1357-1369). (Year: 2013).*
Braisted and Wells (Proc Natl Acad Sci USA 1996, 93:5688-5692) (Year: 1996).*
Uhlen, et al. J. Biol. Chem. 259, 13628, 1984 (Year: 1984).*
Rongxiu Li et al., "Design, synthesis, and application of a Protein A mimetic", Nature Biotechnology, Feb. 1998, pp. 190-195, vol. 16.
Pratima Sinha et al., "Functional Dichotomy of A. 20-MER and 16-MER Peptide Derived From *Staphylococcus aureus* Protein A: Importance of Aminoacid Sequence", Immunopharmacology and Immunotoxicology, 2002, pp. 199-210, vol. 24, No. 2.
Jun Zhang et al., "Protein G, Protein A and Protein-A-Derived Peptides Inhibit the Agitation Induced Aggregation of igG", Molecular Pharmaceutics, Mar. 5, 2012, pp. 622-628, vol. 9, No. 3.
Pratima Sinha et al., "A Minimized Fc Binding Peptide from Protein A Induces Immunocyte Proliferation and Evokes Th1-Type Response in Mice", Biochemical and Biophysical Research Communications, 1999, pp. 141-147, vol. 258, No. 1.
Jayati Sengupta et al., "Molecular Modeling and Experimental Approaches toward Designing a Minimalist Protein Having Fc-binding Activity of *Staphylococcal* Protein A", Biochemical and Biophysical Research Communications, 1999, pp. 6-12, vol. 256, No. 1.
Tomoya Sugita et al., "Screening of peptide ligands that bind to the Fc region of IgG using peptide array and its application to affinity purification of antibody", Biochemical Engineering Journal, Jul. 4, 2013, pp. 33-40, vol. 79.

(Continued)

*Primary Examiner* — Karlheinz R. Skowronek
*Assistant Examiner* — Khalid Kader
(74) *Attorney, Agent, or Firm* — Sughrue Mion, PLLC

(57) ABSTRACT

Provided are an antibody-binding polypeptide as set forth in any one of SEQ ID NOS: 1 to 18 and an adsorption material of an antibody or antibody derivative in which the antibody-binding polypeptide is immobilized on a water-insoluble carrier. These antibody-binding polypeptide and adsorption material have excellent antibody binding properties and selectivity, and also excellent alkali resistance and temporal stability.

11 Claims, No Drawings

Specification includes a Sequence Listing.

(56) References Cited

OTHER PUBLICATIONS

International Search Report for PCT/JP2015/075157 dated Dec. 8, 2015.
Communication dated Jul. 18, 2017, issued by the European Patent Office in counterpart European application No. 15847891.7.
Communication dated Mar. 7, 2018 from the Russian Patent Office in counterpart Application No. 2017110391/04.
International Search Report and Written Opinion, issued by Intellectual Property Office of Singapore in corresponding Application No. 11201702539U dated Dec. 13, 2017.
Canadian Office Action dated Jan. 30, 2018 issued in Canadian Intellectual Property Office in application No. 2962241.
International Preliminary Report on Patentability dated Apr. 13, 2017 issued by the International Bureau in International Application No. PCT/JP2015/075157 with the translation of Written Opinion.
Communication dated Nov. 21, 2017 from the Japanese Patent Office in counterpart Japanese application No. 2016-551675.
Communication dated Jul. 17, 2018, issued by the Korean Intellectual Property Office in corresponding Korean Application No. 10-2017-7008414.
Communication dated Jan. 30, 2019, issued by the Korean Intellectual Property Office in corresponding Korean Application No. 10-2017-7008414.

* cited by examiner

SEQUENCE LISTING

<160> NUMBER OF SEQ ID NOS: 26

<210> SEQ ID NO 1
<211> LENGTH: 7
<212> TYPE: PRT
<213> ORGANISM: Artificial Sequence
<220> FEATURE:
<223> OTHER INFORMATION: polypeptide SeqID No.1: EQQNAFY

<400> SEQUENCE: 1

Glu Gln Gln Asn Ala Phe Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: polypeptide SeqID No.2: KEQQNAFY

<400> SEQUENCE: 2

Lys Glu Gln Gln Asn Ala Phe Tyr

```
<210> SEQ ID NO 3
<211> LENGTH: 11
<212> TYPE: PRT
<213> ORGANISM: Artificial Sequence
<220> FEATURE:
<223> OTHER INFORMATION: polypeptide SeqID No.3: EQQNAFYEILH

<400> SEQUENCE: 3

Glu Gln Gln Asn Ala Phe Tyr Glu Ile Leu His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: polypeptide SeqID No.4: EQQNAFYEILHL

<400> SEQUENCE: 4

Glu Gln Gln Asn Ala Phe Tyr Glu Ile Leu His Leu
1               5                   10

<210> SEQ ID NO 5
<211> LENGTH: 7
<212> TYPE: PRT
<213> ORGANISM: Artificial Sequence
<220> FEATURE:
<223> OTHER INFORMATION: polypeptide SeqID No.5: EGQNAFY

<400> SEQUENCE: 5

Glu Gly Gln Asn Ala Phe Tyr
1               5

<210> SEQ ID NO 6
<211> LENGTH: 13
<212> TYPE: PRT
<213> ORGANISM: Artificial Sequence
<220> FEATURE:
<223> OTHER INFORMATION: polypeptide SeqID No.6: KKKEQQNAFYKKK

<400> SEQUENCE: 6

Lys Lys Lys Glu Gln Gln Asn Ala Phe Tyr Lys Lys Lys
1               5                   10

<210> SEQ ID NO 7
<211> LENGTH: 17
<212> TYPE: PRT
<213> ORGANISM: Artificial Sequence
<220> FEATURE:
<223> OTHER INFORMATION: polypeptide SeqID No.7: KKKEQQNAFYEILHKKK

<400> SEQUENCE: 7

Lys Lys Lys Glu Gln Gln Asn Ala Phe Tyr Glu Ile Leu His Lys Lys
1               5                   10                  15

Lys

<210> SEQ ID NO 8
<211> LENGTH: 21
<212> TYPE: PRT
<213> ORGANISM: Artificial Sequence
<220> FEATURE:
<223> OTHER INFORMATION: polypeptide SeqID No.8: EQQNAFYGGGKGGGEQQNAFY

<400> SEQUENCE: 8
```

Glu Gln Gln Asn Ala Phe Tyr Gly Gly Gly Lys Gly Gly Gly Glu Gln
1               5                   10                  15

Gln Asn Ala Phe Tyr
            20

<210> SEQ ID NO 9
<211> LENGTH: 6
<212> TYPE: PRT
<213> ORGANISM: Artificial Sequence
<220> FEATURE:
<223> OTHER INFORMATION: polypeptide SeqID No.9: EQNAFY

<400> SEQUENCE: 9

Glu Gln Asn Ala Phe Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: polypeptide SeqID No.10: EQQSAFY

<400> SEQUENCE: 10

Glu Gln Gln Ser Ala Phe Tyr
1               5

<210> SEQ ID NO 11
<211> LENGTH: 11
<212> TYPE: PRT
<213> ORGANISM: Artificial Sequence
<220> FEATURE:
<223> OTHER INFORMATION: polypeptide Seq ID No.11: EQQSAFYEILH

<400> SEQUENCE: 11

Glu Gln Gln Ser Ala Phe Tyr Glu Ile Leu His
1               5                   10

<210> SEQ ID NO 12
<211> LENGTH: 7
<212> TYPE: PRT
<213> ORGANISM: Artificial Sequence
<220> FEATURE:
<223> OTHER INFORMATION: polypeptide Seq ID No.12: DQQSAFY

<400> SEQUENCE: 12

Asp Gln Gln Ser Ala Phe Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: polypeptide Seq ID No.13: DQQSAFYEILH

<400> SEQUENCE: 13

Asp Gln Gln Ser Ala Phe Tyr Glu Ile Leu His
1               5                   10

<210> SEQ ID NO 14
<211> LENGTH: 8
<212> TYPE: PRT
<213> ORGANISM: Artificial Sequence
<220> FEATURE:
<223> OTHER INFORMATION: polypeptide Seq ID No.14: EAQQSAFY

```
<400> SEQUENCE: 14

Glu Ala Gln Gln Ser Ala Phe Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: polypeptide Seq ID No.15: EQSAFY

<400> SEQUENCE: 15

Glu Gln Ser Ala Phe Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: polypeptide Seq ID No.16: EAQQNAFY

<400> SEQUENCE: 16

Glu Ala Gln Gln Asn Ala Phe Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: polypeptide Seq ID No.17: DAQQSAFY

<400> SEQUENCE: 17

Asp Ala Gln Gln Ser Ala Phe Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: polypeptide Seq ID No.18: DQSAFY

<400> SEQUENCE: 18

Asp Gln Ser Ala Phe Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: polypeptide Seq ID No.19: EQQNAFY-NH2,
      -NH2- represents C-terminal amidation

<400> SEQUENCE: 19

Glu Gln Gln Asn Ala Phe Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: polypeptide Seq ID No.20: Ac-EQQNAFYK,
      "Ac-" represents N-terminal acetylation
```

-continued

```
<400> SEQUENCE: 20

Glu Gln Gln Asn Ala Phe Tyr Lys
1               5

<210> SEQ ID NO 21
<211> LENGTH: 12
<212> TYPE: PRT
<213> ORGANISM: Artificial Sequence
<220> FEATURE:
<223> OTHER INFORMATION: polypeptide Seq ID No.21: Ac-EQQNAFYEILHK,
      Ac- represents N-terminalacetylation

<400> SEQUENCE: 21

Glu Gln Gln Asn Ala Phe Tyr Glu Ile Leu His Lys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: polypeptide Seq ID No.22: Ac-KKKEQQNAFYKKK,
      Ac- represents N-terminalacetylation

<400> SEQUENCE: 22

Lys Lys Lys Glu Gln Gln Asn Ala Phe Tyr Lys Lys Lys
1               5                   10

<210> SEQ ID NO 23
<211> LENGTH: 17
<212> TYPE: PRT
<213> ORGANISM: Artificial Sequence
<220> FEATURE:
<223> OTHER INFORMATION: polypeptide Seq ID No.23: Ac-KKKEQQNAFYEILHKKK,
      Ac- represents N-terminalacetylation

<400> SEQUENCE: 23

Lys Lys Lys Glu Gln Gln Asn Ala Phe Tyr Glu Ile Leu His Lys Lys
1               5                   10                  15

Lys

<210> SEQ ID NO 24
<211> LENGTH: 8
<212> TYPE: PRT
<213> ORGANISM: Artificial Sequence
<220> FEATURE:
<223> OTHER INFORMATION: polypeptide Seq ID No.24: H2N-(peg)8-EQQNAFYE,
      -(peg)8- represents anocta(ethylene glycol) chain,
      H2N- represents amination

<400> SEQUENCE: 24

Glu Gln Gln Asn Ala Phe Tyr Glu
1               5

<210> SEQ ID NO 25
<211> LENGTH: 15
<212> TYPE: PRT
<213> ORGANISM: Artificial Sequence
<220> FEATURE:
<223> OTHER INFORMATION: polypeptide Seq ID No.25: Ac-EQQNAFY-(peg)8-K-
      (peg)8-EQQNAFY, -(peg)8- represents an octa(ethylene glycol)
      chain, Ac- representsN-terminal acetylation

<400> SEQUENCE: 25

Glu Gln Gln Asn Ala Phe Tyr Lys Glu Gln Gln Asn Ala Phe Tyr
1               5                   10                  15
```

```
<210> SEQ ID NO 26
<211> LENGTH: 8
<212> TYPE: PRT
<213> ORGANISM: Artificial Sequence
<220> FEATURE:
<223> OTHER INFORMATION: polypeptide SeqID_No.26: QQNAFYEI

<400> SEQUENCE: 26

Gln Gln Asn Ala Phe Tyr Glu Ile
1               5
```

ANTIBODY-BINDING POLYPEPTIDE, ANTIBODY-BINDING FUSION POLYPEPTIDE, AND ADSORPTION MATERIAL

CROSS-REFERENCE TO RELATED APPLICATIONS

This application is a Continuation of PCT International Application No. PCT/JP2015/075157 filed on Sep. 4, 2015, which claims priority under 35 U.S.C. § 119(a) to Japanese Patent Application No. 2014-199131 filed on Sep. 29, 2014 and Japanese Patent Application No. 2015-073147 filed on Mar. 31, 2015. Each of the above applications is hereby expressly incorporated by reference, in its entirety, into the present application.

BACKGROUND OF THE INVENTION

1. Field of the Invention

The present invention relates to an antibody-binding polypeptide, an antibody-binding fusion polypeptide, and an adsorption material.

2. Description of the Related Art

In recent years, the development of antibody drugs is booming. This is because antibody drugs making use of human immune function can be expected to have a high efficacy and also exhibit relatively low side effects, whereby such antibody drugs are believed to be as the center of medical treatment in the future. The technology essential to the development and practical applications of antibody drugs is a continuous, large-scale, and high-speed purification technique of antibodies. The currently most commonly used method for the purification of antibodies is affinity chromatography using protein A.

Protein A is a membrane protein present in the cell wall of *Staphylococcus aureus* and is known to have a strong binding ability to the constant region (Fc region, Fc=Fragment, crystallizable) of an antibody molecule. Since common structures are conserved in the constant region across classes and subclasses of various antibody molecules, affinity chromatography using protein A as an antibody-binding ligand can be used for the purification of various kinds of antibody molecules against which antigens are different.

However, since protein A is produced using a genetic engineering method, there is a problem that production processes are complicated, consequently resulting in high production costs. Further, protein A could not be used with several times of repeated washing, due to having insufficient alkali resistance and temporal stability, and a short lifetime resulting from severe degradation caused by alkali washing of a column. For these reasons, costs of antibody purification were likely to be high.

To cope with such problems, for example, Li, R., Dowd, V., Steward, D. J., Burton, S. J., and Lowe, C. R., 1998, Nature Biotechnology, Vol. 16, pp. 190 to 195 discloses a low molecular weight compound ApA (acronym standing for "Artificial protein A") that can be prepared according to the following reaction scheme, from a dipeptide consisting of phenylalanine 132 and tyrosine 133 of protein A as a mimetic ligand for protein A.

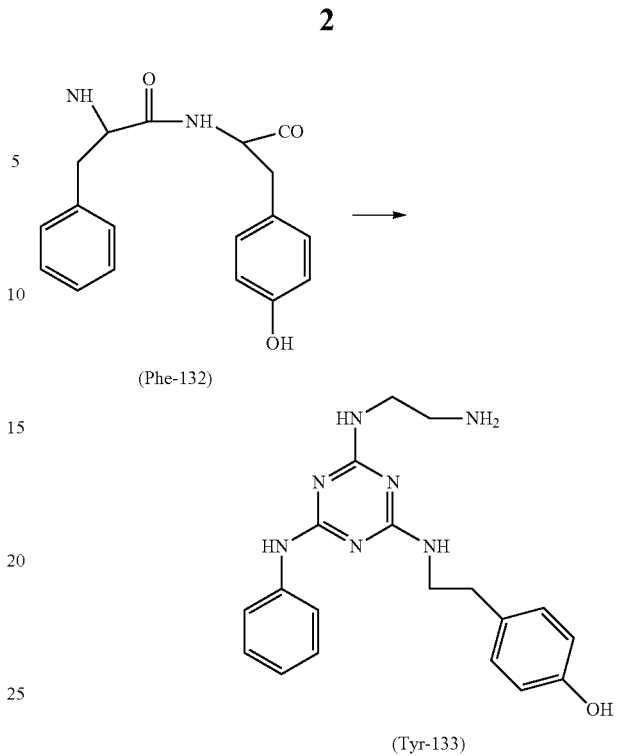

SUMMARY OF THE INVENTION

As will be described in Examples to be given hereinafter, however, according to studies conducted by the present inventors, the low molecular weight compound ApA described in Li, R., Dowd, V., Steward, D. J., Burton, S. J., and Lowe, C. R., 1998, Nature Biotechnology, Vol. 16, pp. 190 to 195 exhibited insufficient antibody binding properties and selectivity, thus failing to satisfy the required level, although having sufficient alkali resistance and temporal stability.

Accordingly, an object of the present invention is to provide an antibody-binding polypeptide and an adsorption material, which have excellent antibody binding properties and selectivity and also excellent alkali resistance and temporal stability.

As a result of extensive studies to solve the foregoing problems, the present inventors have found that an antibody-binding polypeptide as set forth in any one of SEQ ID NOs: 1 to 18 has antibody binding properties and selectivity comparable to protein A, and also exhibits superior alkali resistance and temporal stability. The present invention has been completed based on such a finding.

That is, the present invention provides the following (1) to (13).

(1) An antibody-binding polypeptide as set forth in any one of SEQ ID NOs: 1 to 18.

(2) An antibody-binding polypeptide having a sequence homology of 85% or more to a polypeptide as set forth in any one of SEQ ID NOs: 1to 18.

(3) An antibody-binding polypeptide in which 1 to 10 amino acid residues are covalently bound to at least one place selected from the N-terminal, the C-terminal, and the amino acid side chain of a polypeptide having a sequence homology of 85% or more to a polypeptide as set forth in any one of SEQ ID NOs: 1 to 18.

(4) An antibody-binding polypeptide in which 1 to 24 ethylene glycol units are covalently bound to at least one place selected from the N-terminal, the C-terminal, and the amino acid side chain of a polypeptide having a sequence homology of 85% or more to a polypeptide as set forth in any one of SEQ ID NOs: 1 to 18.

(5) An antibody-binding polypeptide in which at least one place selected from the N-terminal, the C-terminal, and the amino acid side chain of a polypeptide having a sequence homology of 85% or more to a polypeptide as set forth in any one of SEQ ID NOs: 1 to 18 is modified.

(6) An antibody-binding fusion polypeptide in which 2 to 10 domain units are fused by a covalent bond, taking the antibody-binding polypeptide according to any one of (1) to (3) as one domain unit.

(7) An antibody-binding fusion polypeptide in which at least one place selected from the N-terminal, the C-terminal, and the amino acid residue side chain of an antibody-binding fusion polypeptide in which 2 to 10 domain units are fused by a covalent bond, taking the antibody-binding polypeptide according to any one of (1) to (3) as one domain unit, is modified.

(8) The antibody-binding fusion polypeptide according to (6) or (7), in which the antibody-binding fusion polypeptide comprises 2 to 5 foregoing domain units and a linker connecting between the foregoing domain units.

(9) The antibody-binding fusion polypeptide according to (8), in which the linker is at least one linker selected from the group consisting of a peptide linker consisting of 1 to 10 amino acid residues per one linker, a polyethylene glycol (PEG) linker consisting of 1 to 24 ethylene glycol units per one linker, and a complex linker consisting of 1 to 10 amino acid residues and 1 to 24 ethylene glycol units per one linker.

(10) The antibody-binding fusion polypeptide according to (9), in which the linker is at least one linker selected from the group consisting of a peptide linker consisting of 1 to 10 amino acid residues per one linker and a complex linker consisting of 1 to 10 amino acid residues and 1 to 24 ethylene glycol units per one linker, and 1 to 10 amino acid residues include at least one of at least one type amino acid selected from the group consisting of glycine (Gly), alanine (Ala), and serine (Ser).

(11) The antibody-binding fusion polypeptide according to (9), in which the linker is at least one linker selected from the group consisting of a peptide linker consisting of 1 to 10 amino acid residues per one linker and a complex linker consisting of 1 to 10 amino acid residues and 1 to 24 ethylene glycol units per one linker, and 1 to 10 amino acid residues include at least one of at least one type amino acid selected from the group consisting of lysine (Lys), ornithine (Orn), and cysteine (Cys).

(12) The antibody-binding fusion polypeptide according to any one of (9) to (11), in which the total molecular weight of amino acid residues contained in the domain unit and the linker is 5000 or less.

(13) An adsorption material of an antibody or antibody derivative in which the antibody-binding polypeptide according to any one of (1) to (5) or the antibody-binding fusion polypeptide according to any one of (6) to (12) is immobilized on a water-insoluble carrier.

According to the present invention, it is possible to provide an antibody-binding polypeptide which has excellent antibody binding properties and selectivity and also excellent alkali resistance and temporal stability, and an adsorption material of an antibody or antibody derivative which has excellent antibody binding properties and selectivity and also excellent alkali resistance and temporal stability.

Further, according to the present invention, it is possible to build a more robust production process since washing by an alkali or the like can be enhanced in comparison with protein A.

DESCRIPTION OF THE PREFERRED EMBODIMENTS

In the present invention, amino acids are indicated, as a general rule, using names, abbreviations, or the like adopted by the INTERNATIONAL UNION OF PURE AND APPLIED CHEMISTRY and INTERNATIONAL UNION OF BIOCHEMISTRY AND MOLECULAR BIOLOGY IUPAC-IUB Joint Commission on Biochemical Nomenclature (JCBN). The amino acid residues are indicated using abbreviations of amino acids from which the corresponding amino acid residues are derived. Note that the amino acid residue includes an N-terminal amino acid (N-terminal residue) and a C-terminal amino acid (C-terminal residue).

Further, unless otherwise indicated, the amino acid sequence (also referred to as "primary structure") of a polypeptide or protein is set forth such that amino acid residues are arranged in one dimension in the direction of N-terminal to C-terminal in order of left to right ends.

Names and abbreviations (single-letter abbreviations and three-letter abbreviations) of amino acids for which single-letter abbreviations and three-letter abbreviations have been formally accepted are shown in Table 1.

TABLE 1

| Amino acids | Single-letter abbreviations | Three-letter abbreviations |
| --- | --- | --- |
| Alanine | A | Ala |
| Cysteine | C | Cys |
| Aspartic acid | D | Asp |
| Glutamic acid | E | Glu |
| Phenylalanine | F | Phe |
| Glycine | G | Gly |
| Histidine | H | His |
| Isoleucine | I | Ile |
| Lysine | K | Lys |
| Leucine | L | Leu |
| Methionine | M | Met |
| Asparagine | N | Asn |
| Pyrrolysine | O | Pyl |
| Proline | P | Pro |
| Glutamine | Q | Gln |
| Arginine | R | Arg |
| Serine | S | Ser |
| Threonine | T | Thr |
| Selenocysteine | U | Sec |
| Valine | V | Val |
| Tryptophan | W | Trp |
| Tyrosine | Y | Tyr |
| Asp or Asn | B | Asx |
| Glu or Gln | Z | Glx |
| Arbitrary amino acid | X | Xaa |

So-called non-natural amino acids to be described hereinafter, in addition to common amino acids listed in Table 1, may be used as the amino acid.

In the present invention, the term "non-natural amino acid" refers to an amino acid that is naturally not encoded on mRNA. The non-natural amino acid is not particularly limited and examples thereof include 2,3-diaminopropionic acid (Dpr), 2,4-diaminobutyric acid (Dbu), ornithine (Orn), 3-hydroxyproline (3Hyp), 4-hydroxyproline (4Hyp), 2-aminoadipic acid (Aad), 2-aminobutyric acid (Abu), 2-aminoisobutyric acid (Aib), 2-aminopentanoic acid (norvaline; Nva), 2-aminohexanoic acid (norleucine; Nle), 2-aminoheptanoic acid (Ahe), 2-aminopimelic acid (Apm), 2,2'-diaminopimelic acid (Dpm), allohydroxylysine (aHyl), alloisoleucine (aIle), 6-N-methyllysine (MeLys), theanine (2-amino-4-(ethylcarbamoyl)butyric acid), citrulline (2-amino-5-(carbamoylamino)pentanoic acid), desmosine (Des), and isodesmosine (Ide).

In a case where a non-natural amino acid is used, it is preferably used in the linker moiety for binding a polypeptide to a carrier or the linker moiety connecting between domains of a fusion peptide.

In the present invention, the term "domain unit" is a unit on the higher-order structure of a protein or polypeptide and refers to a unit of an amino acid polymer which is composed of a sequence of approximately five to several hundred amino acid residues and is therefore sufficient to express some kinds of physicochemical or biochemical functions.

In the present invention, the term "fusion polypeptide" refers to a polymer compound which is constituted by connecting two or more polypeptides (domain units) having some kinds of physicochemical or biochemical functions directly or via a linker.

In the present invention, the linker connecting between the domain units is not particularly limited, and examples thereof include a peptide linker consisting of peptide units (amino acid residues), a PEG (polyethylene glycol) linker consisting of ethylene glycol units, a disulfide bond (SS bond), and a combination thereof.

In the present invention, the term "antibody" refers to an immunoglobulin or an analogue, fragment or fusion thereof. As used herein, the term "analogue" refers to a natural or artificially constructed protein or protein conjugate in which the structure or function of an immunoglobulin is at least partially retained. Further, the term "fragment" refers to a protein having a partial structure of an immunoglobulin, which has been constructed by an enzymatic treatment or genetic engineering design. Further, the term "fusion" refers to a protein constructed by genetically engineered fusion of the functional part of a protein having a biological activity, such as various cytokines or cytokine receptors, to all or a portion of an immunoglobulin. In addition, the antibody is preferably a monoclonal antibody or a fusion having an Fc region of an immunoglobulin, and more preferably a monoclonal antibody. In the present invention, the immunoglobulin may be any of five classes (isotypes) immunoglobulin G (IgG), immunoglobulin M (IgM), immunoglobulin A (IgA), immunoglobulin D (IgD), and immunoglobulin E (IgE), but it is preferably IgG or IgM and more preferably IgG.

In the present invention, the term "antibody derivative" refers to a chimeric antibody in which an Fc region of a human immunoglobulin is fused to an Fab region of a non-human mammalian immunoglobulin, a chimeric antibody in which several Fc regions of a human immunoglobulin are fused to several Fv regions of a non-human mammalian immunoglobulin, a humanized antibody in which the remaining portion excluding a Complementarity Determining Region (CDR) portion of a human immunoglobulin is fused to a CDR portion of a non-human mammalian immunoglobulin, a chimeric antibody in which an Fc region of non-human mammalian immunoglobulin is fused to an Fab region of a human immunoglobulin, a chimeric antibody in which several Fc regions of a non-human mammalian immunoglobulin are fused to several Fv regions of a human immunoglobulin, a non-human mammalianized antibody in which the remaining portion excluding a CDR portion of a human immunoglobulin is fused to a CDR portion of a non-human mammalian immunoglobulin, a chimeric antibody in which an Fc region of a non-human mammalian immunoglobulin is fused to an Fab region of a non-human mammalian immunoglobulin, a chimeric antibody in which several Fc regions of a non-human mammalian immunoglobulin are fused to several Fv regions of a non-human mammalian immunoglobulin, a non-human mammalian antibody in which the remaining portion excluding a CDR (complementarity determining region) portion of a non-human mammalian immunoglobulin is fused to a CDR portion of a non-human mammalian immunoglobulin, and a protein retaining an Fc region as a protein to which chemical modifications of the foregoing antibodies are added.

In the present invention, the term "antibody binding properties" refers to binding with an antibody or antibody derivative with a certain affinity. The binding with an antibody or antibody derivative is preferably binding by an antigen-antibody reaction, and the site for binding is preferably a constant region (Fc region, $C_L$ region, or $C_H$ region) of an antibody or antibody derivative.

In the present invention, the term "ligand" refers to a molecule that binds to a specific substance with a certain affinity. Examples of such a molecule include a protein, a polypeptide, and a low molecular weight compound. In the present invention, the term "antibody-binding ligand" refers to a ligand having antibody binding properties, that is, a ligand that binds to an antibody or antibody derivative with a certain affinity. In the present invention, the antibody-binding ligand preferably binds to an antibody or antibody derivative through an antigen-antibody reaction by which affinity between specific molecules acts, and the site for binding is preferably a constant region (an Fc region, a $C_L$ region (constant region of light chain), or a $C_H$ region (constant region of heavy chain)) of an antibody or antibody derivative, from the viewpoint of versatility.

[Antibody-binding Polypeptide]

The present invention provides an antibody-binding polypeptide as set forth in any one of SEQ ID NOs: 1 to 18. This antibody-binding polypeptide is a polypeptide that binds to an antibody or antibody derivative with a certain degree of affinity, and binds to the constant region (Fc region) of the antibody or antibody derivative.

Further, the present invention provides an antibody-binding polypeptide having a sequence homology of 85% or more, preferably 87% or more, still more preferably 90% or more, and even more preferably 95% or more to a polypeptide as set forth in any one of SEQ ID NOs: 1to 18.

Here, the sequence homology of two amino acid sequences is determined as follows.

(1) Alignment of two amino acid sequences is carried out.

The alignment is carried out to achieve a maximum alignment score in such a manner that a match is given a score of +1, a mismatch is given a score of −1, and a gap is given a score of −1.

(2) Sequence homology is calculated.

Based on the alignment obtained, the sequence homology is calculated according to the following equation.

Sequence homology [%]=(number of matched positions/number of total positions)×100 [%]

The number of total positions is a length of the alignment, and the number of matched positions is the number of positions where the types of amino acids are matched.

Here, determination of whether or not the types of the amino acid residues are matched will be based on whether or not the structures of side chains of amino acids (amino acid side chains) on which the corresponding amino acid residues are based are identical to each other. The structures of side chains of enantiomeric amino acids are not identical to each other.

(3) Calculation example of sequence homology

For example, consideration is given to the following amino acid sequences.

Sequence A (SEQ ID NO: 1)
EQQNAFY

Sequence B (SEQ ID NO: 2)
KEQQSAFY

When these amino acid sequences are aligned under the conditions described above, it becomes as follows. Here, for the sake of clarity of description, homology string "I" is attached to a place where types of amino acids (residues) are matched between sequences A and B. Further, "-" is a gap.

Sequence A -EQQNAFY
         ||| |||
Sequence B KEQQSAFY

The score of this alignment is match (+1)×6+mismatch (−1)×1+gap (−1)×1=4.

In this example, since the number of total positions is 8 and the number of matched positions is 6, the sequence homology calculated according to the above equation is 6/8×100=75.0%.

Examples of the antibody-binding polypeptide having a sequence homology of 85% or more to a polypeptide (EQQNAFY) as set forth in SEQ ID NO: 1 include a polypeptide (KEQQNAFY, 87.5%) as set forth in SEQ ID NO: 2, a polypeptide (EGQNAFY, 85.7%) as set forth in SEQ ID NO: 5, a polypeptide (EQNAFY, 85.7%) as set forth in SEQ ID NO: 9, a polypeptide (EQQSAFY, 85.7%) as set forth in SEQ ID NO: 10, a polypeptide (EAQQNAFY, 87.5%) as set forth in SEQ ID NO: 16, a polypeptide (EQQNAFY-NH$_2$, 100%) (in which "—NH$_2$" represents amidation of the N-terminal carboxyl group. The same shall apply hereinafter) as set forth in SEQ ID NO: 19, a polypeptide (Ac-EQQNAFYK, 87.5%) (in which "Ac-" represents acetylation of the C-terminal amino group. The same shall apply hereinafter) as set forth in SEQ ID NO: 20, and a polypeptide (H$_2$N-(peg)$_8$-EQQNAFYE, 87.5%) (in which, "peg" represents an ethylene glycol unit, and "H$_2$N-(peg)$_8$-" represents that a polyethylene glycol chain consisting of eight ethylene glycol units having an amino group at the terminal of the side opposite to the side binding to the polypeptide main chain is bonded to the N-terminal amino group. The same shall apply hereinafter) as set forth in SEQ ID NO: 24. Incidentally, the percentage described after the amino acid sequence in bracket represents a sequence homology to a polypeptide as set forth in SEQ ID NO: 1.

Further, examples of the antibody-binding polypeptide having a sequence homology of 87% or more to a polypeptide as set forth in SEQ ID NO: 1 include a polypeptide as set forth in SEQ ID NO:2, a polypeptide as set forth in SEQ ID NO: 16, a polypeptide as set forth in SEQ ID NO: 19, a polypeptide as set forth in SEQ ID NO: 20, and a polypeptide as set forth in SEQ ID NO: 24.

Further, examples of the antibody-binding polypeptide having a sequence homology of 90% or more to a polypeptide as set forth in SEQ ID NO: 1 include a polypeptide as set forth in SEQ ID NO: 19.

Examples of the antibody-binding polypeptide having a sequence homology of 85% or more to a polypeptide (KEQQNAFY) as set forth in SEQ ID NO: 2 include a polypeptide (EQQNAFY, 87.5%) as set forth in SEQ ID NO: 1 and a polypeptide (EQQNAFY-NH$_2$, 87.5%) as set forth in SEQ ID NO: 19. Incidentally, the percentage described after the amino acid sequence in bracket represents a sequence homology to a polypeptide as set forth in SEQ ID NO: 2.

Further, examples of the antibody-binding polypeptide having a sequence homology of 87% or more to a polypeptide as set forth in SEQ ID NO: 2 include a polypeptide as set forth in SEQ ID NO: 1 and a polypeptide as set forth in SEQ ID NO: 19.

Examples of the antibody-binding polypeptide having a sequence homology of 85% or more to a polypeptide (EQQNAFYEILH) as set forth in SEQ ID NO: 3 include a polypeptide (EQQNAFYEILHL, 91.7%) as set forth in SEQ ID NO: 4, a polypeptide (EQQSAFYEILH, 90.9%) as set forth in SEQ ID NO: 11, and a polypeptide (Ac-EQQNAFYEILHK, 91.7%) as set forth in SEQ ID NO: 21. Incidentally, the percentage described after the amino acid sequence in bracket represents a sequence homology to a polypeptide as set forth in SEQ ID NO: 3.

Further, examples of the antibody-binding polypeptide having a sequence homology of 87% or more to a polypeptide as set forth in SEQ ID NO: 3 include a polypeptide as set forth in SEQ ID NO: 4, a polypeptide as set forth in SEQ ID NO: 11, and a polypeptide as set forth in SEQ ID NO: 21.

Further, examples of the antibody-binding polypeptide having a sequence homology of 90% or more to a polypeptide as set forth in SEQ ID NO: 3 include a polypeptide as set forth in SEQ ID NO: 4, a polypeptide as set forth in SEQ ID NO: 11, and a polypeptide as set forth in SEQ ID NO: 21.

Examples of the antibody-binding polypeptide having a sequence homology of 85% or more to a polypeptide (EQQNAFYEILHL) as set forth in SEQ ID NO: 4 include a polypeptide (EQQNAFYEILH, 91.7%) as set forth in SEQ ID NO: 3 and a polypeptide (Ac-EQQNAFYEILHK, 91.7%) as set forth in SEQ ID NO: 21. Incidentally, the percentage described after the amino acid sequence in bracket represents a sequence homology to a polypeptide as set forth in SEQ ID NO: 4.

Further, examples of the antibody-binding polypeptide having a sequence homology of 87% or more to a polypeptide as set forth in SEQ ID NO: 4 include a polypeptide as set forth in SEQ ID NO: 3 and a polypeptide as set forth in SEQ ID NO: 21.

Further, examples of the antibody-binding polypeptide having a sequence homology of 90% or more to a polypeptide as set forth in SEQ ID NO: 4 include a polypeptide as set forth in SEQ ID NO: 3 and a polypeptide as set forth in SEQ ID NO: 21.

Examples of the antibody-binding polypeptide having a sequence homology of 85% or more to a polypeptide (EGQNAFY) as set forth in SEQ ID NO: 5 include a polypeptide (EQQNAFY, 85.7%) as set forth in SEQ ID NO: 1, a polypeptide (EQNAFY, 85.7%) as set forth in SEQ ID NO: 9, and a polypeptide (EQQNAFY-NH$_2$, 85.7%) as set forth in SEQ ID NO: 19. Incidentally, the percentage described after the amino acid sequence in bracket represents a sequence homology to a polypeptide as set forth in SEQ ID NO: 5.

Examples of the antibody-binding polypeptide having a sequence homology of 85% or more to a polypeptide (KKKEQQNAFYKKK) as set forth in SEQ ID NO: 6 include a polypeptide (Ac-KKKEQQNAFYKKK, 100%) as set forth in SEQ ID NO: 22. Incidentally, the percentage described after the amino acid sequence in bracket represents a sequence homology to a polypeptide as set forth in SEQ ID NO: 6.

Further, examples of the antibody-binding polypeptide having a sequence homology of 87% or more to a polypeptide as set forth in SEQ ID NO: 6 include a polypeptide as set forth in SEQ ID NO: 22.

Further, examples of the antibody-binding polypeptide having a sequence homology of 90% or more to a polypeptide as set forth in SEQ ID NO: 6 include a polypeptide as set forth in SEQ ID NO: 22.

Examples of the antibody-binding polypeptide having a sequence homology of 85% or more to a polypeptide (KKKEQQNAFYEILHKKK) as set forth in SEQ ID NO: 7 include a polypeptide (Ac-KKKEQQNAFYEILHKKK, 100%) as set forth in SEQ ID NO: 23. Incidentally, the percentage described after the amino acid sequence in bracket represents a sequence homology to a polypeptide as set forth in SEQ ID NO: 7.

Further, examples of the antibody-binding polypeptide having a sequence homology of 87% or more to a polypeptide as set forth in SEQ ID NO: 7 include a polypeptide as set forth in SEQ ID NO: 23.

Further, examples of the antibody-binding polypeptide having a sequence homology of 90% or more to a polypeptide as set forth in SEQ ID NO: 7 include a polypeptide as set forth in SEQ ID NO: 23.

Examples of the antibody-binding polypeptide having a sequence homology of 85% or more to a polypeptide (EQNAFY) as set forth in SEQ ID NO: 9 include a polypeptide (EQQNAFY, 85.7%) as set forth in SEQ ID NO: 1, a polypeptide (EGQNAFY, 85.7%) as set forth in SEQ ID NO: 5, and a polypeptide (EQQNAFY-NH$_2$, 85.7%) as set forth in SEQ ID NO: 19. Incidentally, the percentage described after the amino acid sequence in bracket represents a sequence homology to a polypeptide as set forth in SEQ ID NO: 9.

Examples of the antibody-binding polypeptide having a sequence homology of 85% or more to a polypeptide (EQQSAFY) as set forth in SEQ ID NO: 10 include a polypeptide (EQQNAFY, 85.7%) as set forth in SEQ ID NO: 1, a polypeptide (DQQSAFY, 85.7%) as set forth in SEQ ID NO: 12, a polypeptide (EAQQSAFY, 87.5%) as set forth in SEQ ID NO: 14, a polypeptide (EQSAFY, 85.7%) as set forth in SEQ ID NO: 15, and a polypeptide (EQQNAFY-NH$_2$, 85.7%) as set forth in SEQ ID NO: 19. Incidentally, the percentage described after the amino acid sequence in bracket represents a sequence homology to a polypeptide as set forth in SEQ ID NO: 10.

Further, examples of the antibody-binding polypeptide having a sequence homology of 87% or more to a polypeptide as set forth in SEQ ID NO: 10 include a polypeptide as set forth in SEQ ID NO: 14.

Examples of the antibody-binding polypeptide having a sequence homology of 85% or more to a polypeptide (EQQSAFYEILH) as set forth in SEQ ID NO: 11 include a polypeptide (EQQNAFYEILH, 90.9%) as set forth in SEQ ID NO: 3 and a polypeptide (DQQSAFYEILH, 90.9%) as set forth in SEQ ID NO: 13. Incidentally, the percentage described after the amino acid sequence in bracket represents a sequence homology to a polypeptide as set forth in SEQ ID NO: 11.

Further, examples of the antibody-binding polypeptide having a sequence homology of 87% or more to a polypeptide as set forth in SEQ ID NO: 11 include a polypeptide as set forth in SEQ ID NO: 3 and a polypeptide as set forth in SEQ ID NO: 13.

Further, examples of the antibody-binding polypeptide having a sequence homology of 90% or more to a polypeptide as set forth in SEQ ID NO: 11 include a polypeptide as set forth in SEQ ID NO: 3 and a polypeptide as set forth in SEQ ID NO: 13.

Examples of the antibody-binding polypeptide having a sequence homology of 85% or more to a polypeptide (DQQSAFY) as set forth in SEQ ID NO: 12 include a polypeptide (EQQSAFY, 85.7%) as set forth in SEQ ID NO: 10, a polypeptide (DAQQSAFY, 87.5%) as set forth in SEQ ID NO: 17, and a polypeptide (DQSAFY, 85.7%) as set forth in SEQ ID NO: 18. Incidentally, the percentage described after the amino acid sequence in bracket represents a sequence homology to a polypeptide as set forth in SEQ ID NO: 12.

Further, examples of the antibody-binding polypeptide having a sequence homology of 87% or more to a polypeptide as set forth in SEQ ID NO: 12 include a polypeptide as set forth in SEQ ID NO: 17.

Examples of the antibody-binding polypeptide having a sequence homology of 85% or more to a polypeptide (DQQSAFYEILH) as set forth in SEQ ID NO: 13 include a polypeptide (EQQSAFYEILH, 90.9%) as set forth in SEQ ID NO: 11. Incidentally, the percentage described after the amino acid sequence in bracket represents a sequence homology to a polypeptide as set forth in SEQ ID NO: 13.

Further, examples of the antibody-binding polypeptide having a sequence homology of 87% or more to a polypeptide as set forth in SEQ ID NO: 13 include a polypeptide as set forth in SEQ ID NO: 11.

Further, examples of the antibody-binding polypeptide having a sequence homology of 90% or more to a polypeptide as set forth in SEQ ID NO: 13 include a polypeptide as set forth in SEQ ID NO: 11.

Examples of the antibody-binding polypeptide having a sequence homology of 85% or more to a polypeptide (EAQQSAFY) as set forth in SEQ ID NO: 14 include a polypeptide (EQQSAFY, 87.5%) as set forth in SEQ ID NO: 10, a polypeptide (EAQQNAFY, 87.5%) as set forth in SEQ ID NO: 16, and a polypeptide (DAQQSAFY, 87.5%) as set forth in SEQ ID NO: 17. Incidentally, the percentage described after the amino acid sequence in bracket represents a sequence homology to a polypeptide as set forth in SEQ ID NO: 14.

Further, examples of the antibody-binding polypeptide having a sequence homology of 87% or more to a polypeptide as set forth in SEQ ID NO: 14 include a polypeptide as set forth in SEQ ID NO: 10, a polypeptide as set forth in SEQ ID NO: 16, and a polypeptide as set forth in SEQ ID NO: 17.

Examples of the antibody-binding polypeptide having a sequence homology of 85% or more to a polypeptide (EQSAFY) as set forth in SEQ ID NO: 15 include a polypeptide (EQQSAFY, 87.5%) as set forth in SEQ ID NO: 10. Incidentally, the percentage described after the amino acid sequence in bracket represents a sequence homology to a polypeptide as set forth in SEQ ID NO: 15.

Examples of the antibody-binding polypeptide having a sequence homology of 85% or more to a polypeptide (EAQQNAFY) as set forth in SEQ ID NO: 16 include a polypeptide (EQQNAFY, 87.5%) as set forth in SEQ ID NO: 1, a polypeptide (EAQQSAFY, 87.5%) as set forth in SEQ ID NO: 14, and a polypeptide (EQQNAFY-NH$_2$, 87.5%) as set forth in SEQ ID NO: 19. Incidentally, the percentage described after the amino acid sequence in bracket represents a sequence homology to a polypeptide as set forth in SEQ ID NO: 16.

Further, examples of the antibody-binding polypeptide having a sequence homology of 87% or more to a polypeptide as set forth in SEQ ID NO: 16 include a polypeptide as set forth in SEQ ID NO: 1, a polypeptide as set forth in SEQ ID NO: 14, and a polypeptide as set forth in SEQ ID NO: 19.

Examples of the antibody-binding polypeptide having a sequence homology of 85% or more to a polypeptide (DAQQSAFY) as set forth in SEQ ID NO: 17 include a polypeptide (DQQSAFY, 87.5%) as set forth in SEQ ID NO: 12 and a polypeptide (EAQQSAFY, 87.5%) as set forth in SEQ ID NO: 14. Incidentally, the percentage described after the amino acid sequence in bracket represents a sequence homology to a polypeptide as set forth in SEQ ID NO: 17.

Further, examples of the antibody-binding polypeptide having a sequence homology of 87% or more to a polypeptide as set forth in SEQ ID NO: 17 include a polypeptide as set forth in SEQ ID NO: 12 and a polypeptide as set forth in SEQ ID NO: 14.

Examples of the antibody-binding polypeptide having a sequence homology of 85% or more to a polypeptide (DQSAFY) as set forth in SEQ ID NO: 18 include a polypeptide (DQQSAFY, 85.7%) as set forth in SEQ ID NO: 12. Incidentally, the percentage described after the amino acid sequence in bracket represents a sequence homology to a polypeptide as set forth in SEQ ID NO: 18.

The antibody-binding polypeptide having a sequence homology of 85% or more to a polypeptide as set forth in any one of SEQ ID NOs: 2 to 4 is preferably an antibody-binding polypeptide with no change in the amino acid sequence of the portion indicated by EQQNAFY in the amino acid sequence, or an antibody-binding polypeptide with a substitution of the amino acid sequence of such a portion to EGQNAFY or EQQSAFY, and more preferably an antibody-binding polypeptide with no change in the amino acid sequence of such a portion.

Further, the present invention provides an antibody-binding polypeptide in which 1 to 10 amino acid residues, and preferably 1 to 5 amino acid residues are each independently covalently bound to at least one place selected from the N-terminal, the C-terminal, and the amino acid side chain of a polypeptide having a sequence homology of 85% or more to a polypeptide as set forth in any one of SEQ ID NOs: 1 to 18.

The above-mentioned amino acid or polypeptide consisting of 1 to 10 amino acid residues can be used, for example, as a linker to a support material (carrier). Examples of the linker to a carrier include Cys having a thiol group, Lys, Orn, Dbu, and Dpr having an amino group, Glu and Asp having a carboxyl group, Ser, Thr, and Tyr having a hydroxyl group, and the others His and Arg. Further, a plurality of those amino acid residues may be used. Further, preferred examples of the amino acid residues to be selected include Cys having a thiol group, Lys, Orn, Dbu, and Dpr having an amino group, Glu and Asp having a carboxyl group, Ser, Thr, and Tyr having a hydroxyl group, and the others His and Arg.

At the terminal or side chain of the side opposite to the side where the above-mentioned linker consisting of 1 to 10 amino acid residues binds to the main chain or side chain of the polypeptide, an immobilizing functional group for immobilization on a carrier may be introduced. Examples of the immobilizing functional group include an amino group, a carboxyl group, a hydroxyl group, and a thiol group.

Examples of the antibody-binding polypeptide in which 1 to 10 amino acid residues, and preferably 1 to 5 amino acid residues are each independently covalently bound to at least one place selected from the N-terminal, the C-terminal, and the amino acid side chain of a polypeptide having a sequence homology of 85% or more to a polypeptide (EQQNAFY) as set forth in SEQ ID NO: 1 include a polypeptide (KK-KEQQNAFYKKK) as set forth in SEQ ID NO: 6. It can be said that this polypeptide is a polypeptide in which "KKK" consisting of 3 amino acid residues is peptide-bound to each of the N-terminal and C-terminal of a polypeptide (EQQNAFY) having a sequence homology of 100% to a polypeptide as set forth in SEQ ID NO: 1.

Examples of the antibody-binding polypeptide in which 1 to 10 amino acid residues, and preferably 1 to 5 amino acid residues are each independently covalently bound to at least one place selected from the N-terminal, the C-terminal, and the amino acid side chain of a polypeptide having a sequence homology of 85% or more to a polypeptide (EQQNAFYEILH) as set forth in SEQ ID NO: 3 include a polypeptide (KKKEQQNAFYEILHKKK) as set forth in SEQ ID NO: 7. It can be said that this polypeptide is polypeptide in which "KKK" consisting of 3 amino acid residues is peptide-bound to each of the N-terminal and C-terminal of a polypeptide (EQQNAFYEILH) having a sequence homology of 100% to a polypeptide as set forth in SEQ ID NO: 3.

Further, the amino acid sequence of the antibody-binding polypeptide in which 1 to 10 amino acid residues, and preferably 1 to 5 amino acid residues are each independently covalently bound to at least one place selected from the N-terminal, the C-terminal, and the amino acid side chain of a polypeptide having a sequence homology of 85% or more to a polypeptide as set forth in SEQ ID NO: 1 preferably does not contain at least one amino acid sequence selected from the group consisting of amino acid sequences as set forth in SEQ ID NOs: 2 to 8, and more preferably does not contain any amino acid sequence.

Further, the amino acid sequence of the polypeptide in which 1 to 10 amino acid residues, and preferably 1 to 5 amino acid residues are each independently covalently bound to at least one place selected from the N-terminal, the C-terminal, and the amino acid side chain of a polypeptide having a sequence homology of 85% or more to a polypeptide as set forth in SEQ ID NO: 2 preferably does not contain at least one amino acid sequence selected from the group consisting of amino acid sequences as set forth in SEQ ID NOs: 6 and 7.

Further, the amino acid sequence of the polypeptide in which 1 to 10 amino acid residues, and preferably 1 to 5 amino acid residues are each independently covalently bound to at least one place selected from the N-terminal, the C-terminal, and the amino acid side chain of a polypeptide having a sequence homology of 85% or more to a polypeptide as set forth in SEQ ID NO: 3 preferably does not contain at least one amino acid sequence selected from the group consisting of amino acid sequences as set forth in SEQ ID NOs: 4 and 7.

Further, the present invention provides an antibody-binding polypeptide in which 1 to 24 ethylene glycol units, and preferably 4 to 8 ethylene glycol units are each independently covalently bound to at least one place selected from the N-terminal, the C-terminal, and the amino acid side chain of a polypeptide having a sequence homology of 85% or more to a polypeptide as set forth in any one of SEQ ID NOs: 1 to 18.

The above-mentioned polyethylene glycol chain consisting of 1 to 24 ethylene glycol units can also be used as a linker to a support material (carrier). In a case where it is used as the linker to a carrier, an immobilizing functional group for immobilization on a carrier may be introduced at the terminal of the side opposite to the side binding to the main chain or side chain of the polypeptide. Examples of the immobilizing functional group include an amino group, a carboxyl group, a hydroxyl group, and a thiol group.

Examples of the antibody-binding polypeptide in which 1 to 24 ethylene glycol units, and preferably 4 to 8 ethylene glycol units are each independently covalently bound to at least one place selected from the N-terminal, the C-terminal, and the amino acid side chain of a polypeptide having a sequence homology of 85% or more to a polypeptide (EQQNAFY) as set forth in SEQ ID NO: 1 include a polypeptide ($H_2N$-(peg)$_8$-EQQNAFYE) as set forth in SEQ ID NO: 24. This polypeptide is a polypeptide in which polyethylene glycol consisting of 8 ethylene glycol units having an amino group at the terminal of the side opposite to the side binding to the polypeptide is covalently bound to the N-terminal of a polypeptide (EQQNAFYE) having a sequence homology of 87.5% to a polypeptide as set forth in SEQ ID NO: 1.

Further, the present invention provides an antibody-binding polypeptide in which at least one place selected from the N-terminal, the C-terminal, and the amino acid side chain of a polypeptide having a sequence homology of 85% or more to a polypeptide as set forth in any one of SEQ ID NOs: 1 to 18 is modified.

The modification is preferably an introduction of a protecting group, or an introduction of an immobilizing functional group for immobilization of a polypeptide on a carrier. Examples of the modification include N-terminal acetylation, addition of Boc (tert-butoxycarbonylation), C-terminal amidation, and esterification. Further, a linker for immobilization on a carrier may be added. For example, attachment of a polyethylene glycol chain consisting of 1 to 24 ethylene glycol units may be exemplified. The terminal of the side opposite to the side binding to the polypeptide of this polyethylene glycol chain may be a hydroxyl group, but an immobilizing functional group such as an amino group, a carboxyl group, or a thiol group may be introduced.

Further, an amino acid side chain may be modified. Examples of the amino acid side chain modification include, but are not particularly limited to, phosphorylation of the side-chain hydroxyl group (Tyr, Ser, or Thr residue), methylation of the side-chain amino group (Lys residue), and acetylation of the side-chain amino group (Lys residue).

The antibody-binding polypeptide of the present invention is preferably a polypeptide as set forth in any one of SEQ ID NOs: 1 to 4, a polypeptide having a sequence homology of 85% or more to such a polypeptide, a polypeptide in which 1 to 10 amino acid residues are each covalently bound to at least one place selected from the N-terminal, the C-terminal, and the amino acid side chain of such a polypeptide, or a polypeptide in which at least one place selected from the N-terminal, the C-terminal, and the amino acid side chain of a polypeptide having a sequence homology of 85% or more to such a polypeptide is modified, more preferably a polypeptide as set forth in SEQ ID NO: 1 or 3, a polypeptide having a sequence homology of 85% or more to such a polypeptide, or a polypeptide in which 1 to 10 amino acid residues are each covalently bound to at least one place selected from the N-terminal, the C-terminal, and the amino acid side chain of such a polypeptide, and still more preferably a polypeptide as set forth in SEQ ID NO: 1, a polypeptide having a sequence homology of 85% or more to such a polypeptide, or a polypeptide in which 1 to 10 amino acid residues are each covalently bound to at least one place selected from the N-terminal, the C-terminal, and the amino acid side chain of such a polypeptide.

Further, the antibody-binding polypeptide of the present invention preferably contains a linker moiety for immobilization on a carrier, and is preferably a polypeptide in which 1 to 10 amino acid residues are each covalently bound to at least one place selected from the N-terminal, the C-terminal, and the amino acid side chain of a polypeptide as set forth in any one of SEQ ID NOs: 1 to 4, more preferably a polypeptide in which 1 to 10 amino acid residues are each covalently bound to at least one place selected from the N-terminal, the C-terminal, and the amino acid side chain of a polypeptide as set forth in SEQ ID NO: 1 or 3, and still more preferably a polypeptide as set forth in SEQ ID NO: 6 or 7.

Particularly preferred is a polypeptide as set forth in SEQ ID NO: 7.

[Antibody-binding Fusion Polypeptide]

Further, the present invention provides an antibody-binding fusion polypeptide in which 2 to 10 domain units are fused by a covalent bond, taking the above-mentioned antibody-binding polypeptide as one domain unit.

By being constructed into an antibody-binding fusion polypeptide, it is possible to enhance the ability to bind to an antibody and an antibody derivative.

At least one place selected from the N-terminal, C-terminal, and amino acid residue side chain of this antibody-binding fusion polypeptide may be modified.

The modification is preferably an introduction of a protecting group, or an introduction of an immobilizing functional group for immobilization of a polypeptide on a carrier. Examples of the modification include N-terminal acetylation, addition of Boc (tert-butoxycarbonylation), C-terminal amidation, and esterification. Further, a linker for immobilization on a carrier may be added. For example, attachment of a polyethylene glycol chain consisting of 1 to 24 ethylene glycol units may be exemplified. The terminal of the side opposite to the side binding to the polypeptide of this polyethylene glycol chain may be a hydroxyl group, but an immobilizing functional group such as an amino group, a carboxyl group, or a thiol group may be introduced.

Further, an amino acid side chain may be modified. Examples of the amino acid side chain modification include, but are not particularly limited to, phosphorylation of the side-chain hydroxyl group (Tyr, Ser, or Thr residue), methylation of the side-chain amino group (Lys residue), and acetylation of the side-chain amino group (Lys residue).

Such an antibody-binding fusion polypeptide may be preferably an antibody-binding fusion polypeptide containing 2 to 5 domain units described above and a linker connecting between domain units.

The linker is not particularly limited as long as it is capable of covalently binding to a polypeptide to thereby connect between domain units. The linker is preferably a linker consisting of amino acid residues and/or ethylene glycol units.

In a case where the linker consists of amino acid residues (peptide units) (hereinafter, the linker consisting of amino acid residues is sometimes referred to as a peptide linker), the number of amino acid residues per one linker is not particularly limited, but it is preferably 1 to 10, and more preferably 1 to 5.

Further, in a case where the linker consists of ethylene glycol units (hereinafter, the linker consisting of ethylene glycol units is sometimes referred to as a PEG linker), the number of ethylene glycol units per one linker is not particularly limited, but it is preferably 1 to 24, more preferably 1 to 12, and still more preferably 4 to 8.

Further, in a case where the linker consists of amino acid residues and ethylene glycol units (hereinafter, the linker consisting of amino acid residues and ethylene glycol units is sometimes referred to as a complex linker), amino acid residues and ethylene glycol units may be bonded randomly or alternately, and one or plural blocks consisting of amino acid residues and one or plural blocks consisting of ethylene glycol units may be connected. The total number of amino acid residues in a case where the linker consists of amino acid residues and ethylene glycol units is not particularly limited, but it is preferably 1 to 10, and more preferably 1 to 5. The total number of ethylene glycol units is also not particularly limited, but it is preferably 1 to 24, more preferably 1 to 12, and still more preferably 4 to 8.

More specifically, preferred is at least one linker selected from the group consisting of a peptide linker consisting of 1 to 10 amino acid residues per one linker, a PEG linker consisting of 1 to 24 ethylene glycol units per one linker, and a complex linker consisting of 1 to 10 amino acid residues and 1 to 24 ethylene glycol units per one linker, more preferred is a peptide linker in which the number of amino acid residues per one linker is 1 to 10, a PEG linker in which the number of ethylene glycol units per one linker is 1 to 24, or a peptide linker in which the number of amino acid residues per one linker is 1 to 10, and still more preferred is a peptide linker in which the number of amino acid residues per one linker is 1 to 5.

Further, in a case of containing two or more linkers, the type and number of amino acid residues and the number of ethylene glycol units in each linker may be the same or different. For example, two or more linkers may be optionally selected and used from the group consisting of a peptide linker, a PEG linker, and a complex linker.

Further, the type of amino acid residues that can be contained in the linker is not particularly limited, and examples thereof include Gly, Ala, and Ser having a low interaction with an IgG antibody. It is preferred to contain at least one of at least one type amino acid residue selected from the group consisting of Gly, Ala, and Ser, per one linker. That is, it is preferred that the linker is at least one linker selected from the group consisting of a peptide linker consisting of 1 to 10 amino acid residues per one linker and a complex linker 1 to 10 amino acid residues and 1 to 24 ethylene glycol units per one linker, and it is more preferred that 1 to 10 amino acid residues include at least one of at least one type amino acid selected from the group consisting of Gly, Ala, and Ser.

Further, the linker may contain one or two or more amino acid residues having a property capable of binding to a carrier. For example, the linker may contain one or two or more amino acid residues selected from the group consisting of Cys having a thiol group, Lys, Orn, Dbu, and Dpr having an amino group, Glu and Asp having a carboxyl group, Ser, Thr, and Tyr having a hydroxyl group, and the others His and Arg.

The molecular weight of the antibody-binding fusion polypeptide of the present invention is not particularly limited. From the viewpoint of antigenicity, the total molecular weight of amino acid residues is preferably 5000 or less, more preferably 3500 or less, and still more preferably 3000 or less.

[Synthesis Method of Polypeptide]

The synthesis method of the polypeptide according to the present invention is not particularly limited. For example, the polypeptide can be synthesized by an organic synthetic chemical peptide synthesis method or a genetic engineering peptide synthesis method.

Any of a liquid-phase synthesis method and a solid-phase synthesis method can be used as the organic synthetic chemical peptide synthesis method. As the synthesis method of the polypeptide according to the present invention, a solid-phase synthesis method using an automated peptide synthesizer is convenient and preferable.

The genetic engineering peptide synthesis method is a method for synthesizing a peptide by gene transfer into cells. The cells that can be used include bacteria, nematode cells, insect cells, mammalian cells, animal cells, and the like.

[Adsorption Material of Antibody or Antibody Derivative]

Further, the present invention provides an adsorption material of an antibody or antibody derivative in which the above-mentioned antibody-binding polypeptide or the above-mentioned antibody-binding fusion polypeptide is immobilized on a water-insoluble carrier. Further, the present invention may also provide an affinity chromatographic carrier using this adsorption material.

Examples of the above-mentioned water-insoluble carrier include polysaccharides such as crystalline cellulose, crosslinked cellulose, crosslinked agarose, crosslinked dextran, and crosslinked pullulan; organic carriers such as acrylate-based polymers and styrene-based polymers; inorganic carriers such as glass beads and silica gels; and composite carriers obtained by combining these carriers, such as organic-organic carriers and organic-inorganic carriers. From the viewpoint of alkali resistance, the water-insoluble carrier is more preferably a polysaccharide or acrylate-based polymer, and still more preferably a polysaccharide such as agarose or cellulose. Examples of commercially available products that can be used as the water-insoluble carrier include Cellufine GCL2000 (manufactured by JNC Corporation) and Cellufine MAX CM (manufactured by JNC Corporation) each of which is a porous cellulose gel, Sephacryl S-1000 SF (manufactured by GE Healthcare) which is a covalently crosslinked product of allyl dextran with methylene bisacrylamide, TOYOPEARL (manufactured by Tosoh Corporation), TOYOPEARL AF-Carboxy-650 (manufactured by Tosoh Corporation), and TOYOPEARL GigaCap CM-650 (manufactured by Tosoh Corporation) each of which is an acrylate-based carrier, Sepharose CL4B (manufactured by GE Healthcare) which is an agarose-based crosslinked carrier, and Eupergit C250L (manufactured by Sigma-Aldrich) which is an polymethacrylamide activated with an epoxy group. However, the water-insoluble carrier in the present invention is not limited to these carriers or activated carriers. Further, in the light of the intended use of and how to use the present adsorption material, the water-insoluble carrier used in the present invention is preferably a water-insoluble carrier having a large surface area and is preferably a porous water-insoluble carrier having a large number of pores having a suitable size. The shape of the carrier is not particularly limited and may be any of being bead-like, fiber-like, film-like, hollow fiber-like, and the like from which any shape may be selected.

[Method for Immobilization on Carrier]

Although the method for immobilizing the antibody-binding polypeptide or antibody-binding fusion polypeptide of the present invention on a water-insoluble carrier is not particularly limited, the method employed typically in a case where a protein or polypeptide is immobilized on a carrier will be illustrated.

Examples of such an immobilization method include an immobilization method in which a carrier is reacted with cyanogen bromide, epichlorohydrin, diglycidyl ether, tosyl chloride, tresyl chloride, hydrazine or the like to activate a carrier or introduce a reactive functional group onto the carrier surface, and then the carrier is reacted with an immobilization compound as a ligand to immobilize it on the carrier, and an immobilization method in which a condensation agent such as carbodiimide or a reagent having a plurality of functional groups in the molecule, such as glyceraldehyde, is added to a system where a carrier and an immobilization compound as a ligand are present, followed by condensation and crosslinking.

When a ligand is immobilized on a carrier, it is preferred to dissolve (disperse) the ligand in an aqueous solvent (aqueous dispersion medium) or an organic solvent (organic dispersion medium). The aqueous solvent (aqueous dispersion medium) is not particularly limited, and examples thereof include HEPES buffer, acetate buffer, phosphate buffer, citrate buffer, and Tris-HCl buffer. The organic solvent (organic dispersion medium) is not particularly limited, but it is preferably a polar organic solvent, particularly preferably dimethyl sulfoxide (DMSO) or dimethylformamide (DMF), or an alcohol, examples of which include methanol, ethanol, 2-propanol (IPA, isopropyl alcohol), 2,2,2-trifluoroethanol (TFE, trifluoroethanol), and 1,1,1,3,3,3-hexafluoro-2-propanol (HFIP, hexafluoroisopropyl alcohol).

The pH conditions at the time of immobilizing a ligand are not particularly limited and may be acidic, neutral, or alkaline. For example, the pH conditions may be appropriately set in accordance with a solvent (dispersion medium) to be used.

For example, in a case where the pH conditions are alkaline, a base such as diazabicycloundecene (DBU) may be added to DMSO or alcohol.

The density of the antibody-binding ligand in a case where the above-mentioned adsorption material is served as a packing material for affinity chromatography is not particularly limited, but it is preferably 0.1 to 1000 mmol/1 L packing material, more preferably 0.1 to 500 mmol/1 L packing material, and still more preferably 1 to 100 mmol/1 L packing material. When the density of the antibody-binding ligand is within this range, antibodies can be efficiently purified at a lower cost with good balance between the used amount of the antibody-binding ligand and the antibody purification performance.

[Molecular Weight of Ligand]

In addition, although it is known that a molecule having a large molecular weight, such as protein A or Z fragment of protein A, has antigenicity, it is also known that a molecule having a small molecular weight with the total molecular weight of amino acid residues being typically 5000 or less, preferably 3500 or less, and more preferably 3000 or less hardly expresses antigenicity. The antibody-binding polypeptide of the present invention hardly expresses antigenicity, and therefore a ligand-immobilized carrier in which such an antibody-binding polypeptide has been immobilized on a carrier is preferably used as an affinity chromatographic carrier.

[Uses of Antibody-binding Polypeptide]

With respect to uses of the antibody-binding polypeptide of the present invention, there are a use as an antibody-binding ligand in the technical field of the above-mentioned affinity chromatography, a use as a linker for labeling an antibody in the technical field of immunoassay, and a use as a linker for an antibody drug conjugate in the technical field of an antibody drug conjugate.

<Linker for Labeling Antibody>

Immunoassay is an analytical method for performing detection and quantification of trace substances using an immune reaction (antigen-antibody reaction), and has characteristics of high specificity and high sensitivity.

With respect to immunoassay, in detecting an antibody (primary antibody) bound to a trace substance (antigen), there is a method of directly labeling a primary antibody, a method of labeling an antibody (secondary antibody) that binds to a primary antibody, or the like. The antibody-binding polypeptide of the present invention may be used as a linker for binding a labeling substance to a primary antibody and may also be used as a linker for binding a labeling substance to a secondary antibody. Since the antibody-binding polypeptide of the present invention has antibody binding properties (IgG binding properties), it is possible to use the labeled antibody-binding polypeptide of the present invention in place of the labeled secondary antibody.

In addition, there is a wide variety of labels. The system using a radioisotope as a label system is referred to as radioimmunoassay (RIA), the system using an enzyme, such as peroxidase, as a label is referred to as enzyme immunoassay (EIA), the system using a chemiluminescent substance, such as luminal, as a label is referred to as chemiluminescent immunoassay (CLIA), and the system using a fluorescence-emitting substance (fluorescent dye), such as fluorescein isothiocyanate (FITC), as a label is referred to as fluorescent immunoassay (FIA). The antibody-binding polypeptide of the present invention can be used in any of the systems, as a linker for labeling an antibody.

In order to increase the detection sensitivity of immunoassay, it is necessary to label a single molecule of antibody with a large number of labels, but in conventional linkers for labeling an antibody, there was a possibility that binding of a large number of labels leads to a decrease in binding activity of the antibody, thus deteriorating specificity and sensitivity which are advantages of immunoassay. However, with respect to the antibody-binding polypeptide of the present invention, even in a case where a large number of such antibody-binding polypeptides are bound to an antibody, it is expected to increase the detection sensitivity without deteriorating specificity and sensitivity which are advantages of immunoassay even when a large number of such antibody-binding polypeptides are bound, since the structural integrity of the antibody can be retained and therefore the binding activity of the antibody is not decreased.

<Linker for Antibody Drug Conjugate>

The antibody drug conjugate (ADC) is also referred to as an armed antibody which is another name, and is a medicine in which an antibody recognizing cells and an active main body, drug (small molecular weight drug) are coupled via a suitable linker. The action mechanism of an antibody drug conjugate is schematically as follows.

(1) The antibody portion of the antibody drug conjugate binds to a target molecule of the target cell surface.

(2) The antibody drug conjugate is taken into cells.

(3) The linker of the antibody drug conjugate is cleaved intracellularly.

(4) The drug efficacy of the drug (small molecular weight drug) is exerted in cells.

With the antibody drug conjugate, since the drug efficacy is exerted only in cells expressing a molecule to be targeted by an antibody, systemic side effects are inhibited and drug efficacy can be focused and exerted on target cells, so the antibody drug conjugate exhibits better effects and less side effects as compared to a drug alone. For example, since anticancer agents developed for the purpose of attacking cancer cells exhibiting active cell division would also attack the cells retaining functions by active cell division in the same manner, specifically cells responsible for immunity, cells of the gastrointestinal tract, cells of the hair root or the like, there may be some cases where symptoms such as vulnerability to infections, diarrhea, and loss of scalp hair are exhibited as side effects. However, with the antibody drug conjugate, it is possible to deliver an anticancer agent selectively to target cancer cells, so it is possible to suppress the side effects caused by attack of the anticancer agent on the cells other than the target cells.

The linker for an antibody drug conjugate is required to not only satisfy that the antibody portion and the drug portion of the antibody drug conjugate are connected and stable in blood, and the antibody and the drug are cleaved and released intracellularly, but also satisfy that the binding activity of the antibody is not impaired. In order to increase delivery efficiency of a drug, it is necessary to label a single molecule of antibody with a large number of drugs, but in conventional linkers for an antibody drug conjugate, there was a possibility that binding of a large number of drugs leads to a decrease in binding activity of the antibody, thus deteriorating selectivity which is an advantage of the antibody drug conjugate, whereby the drug delivery efficiency to target cells would be decreased. However, with respect to the antibody-binding polypeptide of the present invention, even in a case where a large number of such antibody-binding polypeptides are bound to an antibody, it is expected to increase the drug delivery efficiency to target cells without deteriorating selectivity which is an advantage of the antibody drug conjugate even when a large number of such antibody-binding polypeptides are bound, since the structural integrity of the antibody can be retained and therefore the binding activity of the antibody is not decreased.

EXAMPLES

The present invention will be described in more detail with reference to the following Examples, but the present invention is not limited thereto.

[Synthesis of Polypeptide]

The polypeptides or fusion polypeptides of SEQ ID NO: 1 to SEQ ID NO: 20 shown in Table 2 were synthesized by a fully automated peptide synthesizer (PSSM-8, manufactured by Shimadzu Corporation).

Example 1

(1) Immobilization of Ligand

A commercially available CM5 (carboxymethyl dextran introduction type, manufactured by GE Healthcare) sensor chip was set on a surface plasmon resonance (SPR) apparatus Biacore (manufactured by GE Healthcare), HEPES buffer (20 mM HEPES-HCl, 150 mM NaCl, pH 7.4) for SPR was stabilized at a flow rate of 10 μL/min, and 70 μL of a mixed aqueous solution of 0.2 M 1-ethyl-3-(3-dimethylaminopropyl)carbodiimide (EDC, manufactured by Wako Pure Chemical Industries, Ltd.) and 0.04 M N-hydroxysuccinimide (NHS, manufactured by Wako Pure Chemical Industries, Ltd.) was added. Then, 500 μL of a sample solution of polypeptide 1 diluted to 100 μM with the above-mentioned HEPES buffer and treated with a 0.20 μm PTFE filter (manufactured by ADVANTEC) was supplied to a carrier sample, blocked by an ethanolamine solution, and washed with an aqueous sodium hydroxide solution, followed by immobilization to prepare an immobilized carrier. This immobilized carrier is hereinafter referred to as "immobilized carrier A".

(2) Evaluation of Antibody Binding Properties 10 to 3000 nM of a human IgG antibody was added to the immobilized carrier A prepared in the above (1) over 10 min, and the dissociation at 25° C. in HEPES buffer was measured. The association rate Kon [nM/s] and the dissociation rate Koff [l/s] of an antibody were calculated from the binding reaction curve, and also the dissociation constant Kd [nM] in the binding reaction of polypeptide 1 with a human IgG antibody was calculated.

(Evaluation Standards of Antibody Binding Properties)

| | |
|---|---|
| The dissociation constant (Kd) is 100 nM or less | A |
| The dissociation constant (Kd) is greater than 100 nM and 300 nM or less | B |
| The dissociation constant (Kd) is greater than 300 nM and 500 nM or less | C |
| The dissociation constant (Kd) is greater than 500 nM and 1000 nM or less | D |
| The dissociation constant (Kd) is greater than 1000 nM | E |

The evaluation results are shown in the corresponding column of Table 2.

Evaluations A and B indicate that the ligand has sufficient antibody binding properties as a ligand for an affinity chromatographic carrier, and Evaluations C, D and E indicate that the ligand does not have sufficient antibody binding properties. By using a ligand having sufficient antibody binding properties, the recovery efficiency is increased and it has become possible to more efficiently purify antibodies, whereby purification costs of antibodies can be further reduced.

Fitting was carried out using a BIAevaluation4.1 (fitting software, manufactured by GE Healthcare), and the thus-calculated dissociation rate Koff was $1.7 \times 10^{-4}$ [l/s].

(3) Evaluation of Selectivity 1000 nM of Bovine Serum Albumin (BSA, manufactured by Sigma-Aldrich) was added to the immobilized carrier A prepared in the above (1) at 25° C. over 10 min, and the binding amount after 10 minutes in HEPES buffer was measured by SPR.

(Evaluation Standards of Selectivity)

| | |
|---|---|
| Not bound to BSA | A |
| Confirmed to be bound to BSA | D |

The evaluation results are shown in the corresponding column of Table 2.

Evaluation A indicates that the ligand has a sufficient selectivity as a ligand for an affinity chromatographic carrier, and Evaluation D indicates that the ligand does not have a sufficient selectivity. By using a ligand having a sufficient selectivity, a probability of a protein other than a desired antibody to bind to a ligand is decreased, whereby more highly purified antibodies can be obtained.

(4) Evaluation of Alkali Resistance

The synthesized polypeptide 1 was immersed in 1N NaOH at room temperature for 1 hour, and then the ligand was immobilized as in the above (1). Whether or not the antibody-binding amount of the thus-prepared immobilized carrier A had been changed was evaluated by SPR.

(Evaluation Standards of Alkali Resistance)

| The antibody-binding amount was not changed | A |
|---|---|
| The antibody-binding amount was decreased | D |

The evaluation results are shown in the corresponding column of Table 2.

Evaluation A indicates that the ligand has a sufficient alkali resistance as a ligand for an affinity chromatographic carrier, and Evaluation D indicates that the ligand does not have sufficient alkali resistance. By using a ligand having a sufficient alkali resistance, it is possible to use an affinity chromatographic carrier with repeated washing, whereby purification costs of antibodies can be reduced.

(5) Evaluation of Temporal Stability

A solution of the synthesized polypeptide 1 was stored in a constant-temperature zone (40° C.) for one month, and then the ligand was immobilized as in the above (1). Whether or not the antibody-binding amount of the thus-prepared immobilized carrier A had been changed was evaluated by SPR.

(Evaluation Standards of Temporal Stability)

| The antibody-binding amount was not changed | A |
|---|---|
| Tne antibody-binding amount was decreased | D |

Evaluation A indicates that the ligand has a sufficient temporal stability as a ligand for an affinity chromatographic carrier, and Evaluation D indicates that the ligand does not have sufficient temporal stability. By using a ligand having a sufficient temporal stability, an affinity chromatographic carrier can be stored under room temperature conditions and can be repeatedly used, whereby purification costs of antibodies can be reduced.

Example 2

(1) An "immobilized carrier B" was prepared in the same manner as in Example 1, except that a polypeptide as set forth in SEQ ID NO: 2 was used in place of a polypeptide as set forth in SEQ ID NO: 1 as a ligand.

(2) Using the thus-prepared immobilized carrier B and in the same manner as in Example 1, antibody binding properties, selectivity, alkali resistance, and temporal stability were evaluated. The evaluation results are shown in the corresponding column of Table 2.

Further, the dissociation rate Koff was $1.3 \times 10^{-4}$ [l/s].

Example 3

(1) An "immobilized carrier C" was prepared in the same manner as in Example 1, except that a polypeptide as set forth in SEQ ID NO: 3 was used in place of a polypeptide as set forth in SEQ ID NO: 1 as a ligand.

(2) Using the thus-prepared immobilized carrier C and in the same manner as in Example 1, antibody binding properties, selectivity, alkali resistance, and temporal stability were evaluated. The evaluation results are shown in the corresponding column of Table 2.

Further, the dissociation rate Koff was $1.7 \times 10^{-4}$ [l/s].

Example 4

(1) An "immobilized carrier D" was prepared in the same manner as in Example 1, except that a polypeptide as set forth in SEQ ID NO: 4 was used in place of a polypeptide as set forth in SEQ ID NO: 1 as a ligand.

(2) Using the thus-prepared immobilized carrier D and in the same manner as in Example 1, antibody binding properties, selectivity, alkali resistance, and temporal stability were evaluated. The evaluation results are shown in the corresponding column of Table 2.

Further, the dissociation rate Koff was $1.3 \times 10^{-4}$ [l/s].

Example 5

(1) An "immobilized carrier E" was prepared in the same manner as in Example 1, except that a polypeptide as set forth in SEQ ID NO: 5 was used in place of a polypeptide as set forth in SEQ ID NO: 1 as a ligand.

(2) Using the thus-prepared immobilized carrier E and in the same manner as in Example 1, antibody binding properties, selectivity, alkali resistance, and temporal stability were evaluated. The evaluation results are shown in the corresponding column of Table 2.

Further, the dissociation rate Koff was $2.0 \times 10^{-4}$ [l/s].

Example 6

(1) An "immobilized carrier F" was prepared in the same manner as in Example 1, except that a polypeptide as set forth in SEQ ID NO: 6 was used in place of a polypeptide as set forth in SEQ ID NO: 1 as a ligand, and 50 µL of a sample solution diluted to 25 µM with an acetate buffer of pH 4.0 was used in place of 500 µL of a sample solution diluted to 100 µM with a HEPES buffer.

(2) Using the thus-prepared immobilized carrier F and in the same manner as in Example 1, antibody binding properties, selectivity, alkali resistance, and temporal stability were evaluated. The evaluation results are shown in the corresponding column of Table 2.

Further, the dissociation rate Koff was $1.5 \times 10^{-4}$ [l/s].

Example 7

(1) An "immobilized carrier G" was prepared in the same manner as in Example 1, except that a polypeptide as set forth in SEQ ID NO: 7 was used in place of a polypeptide as set forth in SEQ ID NO: 1 as a ligand, and 50 µL of a sample solution diluted to 25 µM with an acetate buffer of pH 4.0 was used in place of 500 µL of a sample solution diluted to 100 µM with a HEPES buffer.

(2) Using the thus-prepared immobilized carrier G and in the same manner as in Example 1, antibody binding properties, selectivity, alkali resistance, and temporal stability were evaluated. The evaluation results are shown in the corresponding column of Table 2.

Further, the dissociation rate Koff was $1.6 \times 10^{-4}$ [l/s].

Example 8

(1) An "immobilized carrier H" was prepared in the same manner as in Example 1, except that a polypeptide as set forth in SEQ ID NO: 8 was used in place of a polypeptide as set forth in SEQ ID NO: 1 as a ligand.

(2) Using the thus-prepared immobilized carrier H and in the same manner as in Example 1, antibody binding properties, selectivity, alkali resistance, and temporal stability were evaluated. The evaluation results are shown in the corresponding column of Table 2.

Further, the dissociation rate Koff was $1.5 \times 10^{-4}$ [l/s].

Example 9

(1) An "immobilized carrier I" was prepared in the same manner as in Example 1, except that a polypeptide as set forth in SEQ ID NO: 9 was used in place of a polypeptide as set forth in SEQ ID NO: 1 as a ligand.

(2) Using the thus-prepared immobilized carrier I and in the same manner as in Example 1, antibody binding properties, selectivity, alkali resistance, and temporal stability were evaluated. The evaluation results are shown in the corresponding column of Table 2.

Further, the dissociation rate Koff was $1.7 \times 10^{-4}$ [l/s].

Example 10

(1) An "immobilized carrier J" was prepared in the same manner as in Example 1, except that a polypeptide as set forth in SEQ ID NO: 10 was used in place of a polypeptide as set forth in SEQ ID NO: 1 as a ligand, and 50 µL of a sample solution diluted to 25 µM with an acetate buffer of pH 4.0 was used in place of 500 µL of a sample solution diluted to 100 µM with a HEPES buffer.

(2) Using the thus-prepared immobilized carrier J and in the same manner as in Example 1, antibody binding properties, selectivity, alkali resistance, and temporal stability were evaluated. The evaluation results are shown in the corresponding column of Table 2.

Further, the dissociation rate Koff was $1.5 \times 10^{-4}$ [l/s].

Example 11

(1) An "immobilized carrier K" was prepared in the same manner as in Example 1, except that a polypeptide as set forth in SEQ ID NO: 11 was used in place of a polypeptide as set forth in SEQ ID NO: 1 as a ligand, and 50 µL of a sample solution diluted to 25 µM with an acetate buffer of pH 4.0 was used in place of 500 µL of a sample solution diluted to 100 µM with a HEPES buffer.

(2) Using the thus-prepared immobilized carrier K and in the same manner as in Example 1, antibody binding properties, selectivity, alkali resistance, and temporal stability were evaluated. The evaluation results are shown in the corresponding column of Table 2.

Further, the dissociation rate Koff was $1.8 \times 10^{-4}$ [l/s].

Example 12

(1) An "immobilized carrier L" was prepared in the same manner as in Example 1, except that a polypeptide as set forth in SEQ ID NO: 12 was used in place of a polypeptide as set forth in SEQ ID NO: 1 as a ligand, and 50 µL of a sample solution diluted to 25 µM with an acetate buffer of pH 4.0 was used in place of 500 µL of a sample solution diluted to 100 µM with a HEPES buffer.

(2) Using the thus-prepared immobilized carrier L and in the same manner as in Example 1, antibody binding properties, selectivity, alkali resistance, and temporal stability were evaluated. The evaluation results are shown in the corresponding column of Table 2.

Further, the dissociation rate Koff was $1.5 \times 10^{-4}$ [l/s].

Example 13

(1) An "immobilized carrier M" was prepared in the same manner as in Example 1, except that a polypeptide as set forth in SEQ ID NO: 13 was used in place of a polypeptide as set forth in SEQ ID NO: 1 as a ligand, and 50 µL of a sample solution diluted to 25 µM with an acetate buffer of pH 4.0 was used in place of 500 µL of a sample solution diluted to 100 µM with a HEPES buffer.

(2) Using the thus-prepared immobilized carrier M and in the same manner as in Example 1, antibody binding properties, selectivity, alkali resistance, and temporal stability were evaluated. The evaluation results are shown in the corresponding column of Table 2.

Further, the dissociation rate Koff was $1.5 \times 10^{-4}$ [l/s].

Example 14

(1) An "immobilized carrier N" was prepared in the same manner as in Example 1, except that a polypeptide as set forth in SEQ ID NO: 14 was used in place of a polypeptide as set forth in SEQ ID NO: 1 as a ligand, and 50 µof a sample solution diluted to 25 µM with an acetate buffer of pH 4.0 was used in place of 500 µL of a sample solution diluted to 100 µM with a HEPES buffer.

(2) Using the thus-prepared immobilized carrier N and in the same manner as in Example 1, antibody binding properties, selectivity, alkali resistance, and temporal stability were evaluated. The evaluation results are shown in the corresponding column of Table 2.

Further, the dissociation rate Koff was $1.4 \times 10^{-4}$ [l/s].

Example 15

(1) An "immobilized carrier O " was prepared in the same manner as in Example 1, except that a polypeptide as set forth in SEQ ID NO: 15 was used in place of a polypeptide as set forth in SEQ ID NO: 1 as a ligand, and 50 µof a sample solution diluted to 25 µM with an acetate buffer of pH 4.0 was used in place of 500 µL of a sample solution diluted to 100 µM with a HEPES buffer.

(2) Using the thus-prepared immobilized carrier O and in the same manner as in Example 1, antibody binding properties, selectivity, alkali resistance, and temporal stability were evaluated. The evaluation results are shown in the corresponding column of Table 2.

Further, the dissociation rate Koff was $1.4 \times 10^{-4}$ [l/s].

Example 16

(1) An "immobilized carrier P" was prepared in the same manner as in Example 1, except that a polypeptide as set forth in SEQ ID NO: 16 was used in place of a polypeptide as set forth in SEQ ID NO: 1 as a ligand, and 50 µL of a sample solution diluted to 25 µM with an acetate buffer of pH 4.0 was used in place of 500 µL of a sample solution diluted to 100 µM with a HEPES buffer.

(2) Using the thus-prepared immobilized carrier P and in the same manner as in Example 1, antibody binding properties, selectivity, alkali resistance, and temporal stability were evaluated. The evaluation results are shown in the corresponding column of Table 2.

Further, the dissociation rate Koff was $1.9 \times 10^{-4}$ [l/s].

Example 17

(1) An "immobilized carrier Q" was prepared in the same manner as in Example 1, except that a polypeptide as set forth in SEQ ID NO: 17 was used in place of a polypeptide as set forth in SEQ ID NO: 1 as a ligand, and 50 µL of a sample solution diluted to 25 µM with an acetate buffer of pH 4.0 was used in place of 500 μL of a sample solution diluted to 100 μM with a HEPES buffer.

(2) Using the thus-prepared immobilized carrier Q and in the same manner as in Example 1, antibody binding properties, selectivity, alkali resistance, and temporal stability were evaluated. The evaluation results are shown in the corresponding column of Table 2.

Further, the dissociation rate Koff was $1.3 \times 10^{-4}$ [1/s].

Example 18

(1) An "immobilized carrier R" was prepared in the same manner as in Example 1, except that a polypeptide as set forth in SEQ ID NO: 18 was used in place of a polypeptide as set forth in SEQ ID NO: 1 as a ligand, and 50 μL of a sample solution diluted to 25 μM with an acetate buffer of pH 4.0 was used in place of 500 μL of a sample solution diluted to 100 μM with a HEPES buffer.

(2) Using the thus-prepared immobilized carrier R and in the same manner as in Example 1, antibody binding properties, selectivity, alkali resistance, and temporal stability were evaluated. The evaluation results are shown in the corresponding column of Table 2.

Further, the dissociation rate Koff was $1.9 \times 10^{-4}$ [1/s].

Example 19

(1) An "immobilized carrier S" was prepared in the same manner as in Example 1, except that a polypeptide having a primary structure shown in the column "Ligand" of Example 19 in Table 2 was used in place of a polypeptide as set forth in SEQ ID NO: 1 as a ligand.

In the column "Ligand" of Example 19 in Table 2, "-NH$_2$" at the C-terminal of the primary structure indicates that the carboxy group of a tyrosine residue at the C-terminal is amidated.

(2) Using the thus-prepared immobilized carrier S and in the same manner as in Example 1, antibody binding properties, selectivity, alkali resistance, and temporal stability were evaluated. The evaluation results are shown in the corresponding column of Table 2.

Further, the dissociation rate Koff was $1.5 \times 10^{-4}$ [1/s].

Example 20

(1) An "immobilized carrier T" was prepared in the same manner as in Example 1, except that a polypeptide having a primary structure shown in the column "Ligand" of Example 20 in Table 2 was used in place of a polypeptide as set forth in SEQ ID NO: 1 as a ligand.

In the column "Ligand" of Example 20 in Table 2, "Ac-" at the N-terminal of the primary structure indicates that the amino group bonded to an a-position carbon of a glutamine residue at the N-terminal is acetylated.

(2) Using the thus-prepared immobilized carrier T and in the same manner as in Example 1, antibody binding properties, selectivity, alkali resistance, and temporal stability were evaluated. The evaluation results are shown in the corresponding column of Table 2.

Further, the dissociation rate Koff was $1.4 \times 10^{-4}$ [1/s].

Example 21

(1) An "immobilized carrier U" was prepared in the same manner as in Example 1, except that a polypeptide having a primary structure shown in the column "Ligand" of Example 21 in Table 2 was used in place of a polypeptide as set forth in SEQ ID NO: 1 as a ligand.

In the column "Ligand" of Example 21 in Table 2, "Ac-" at the N-terminal of the primary structure indicates that the amino group bonded to an a-position carbon of a glutamine residue at the N-terminal is acetylated.

(2) Using the thus-prepared immobilized carrier U and in the same manner as in Example 1, antibody binding properties, selectivity, alkali resistance, and temporal stability were evaluated. The evaluation results are shown in the corresponding column of Table 2.

Further, the dissociation rate Koff was $1.6 \times 10^{-4}$ [1/S].

Example 22

(1) An "immobilized carrier V" was prepared in the same manner as in Example 1, except that a polypeptide having a primary structure shown in the column "Ligand" of Example 22 in Table 2 was used in place of a polypeptide as set forth in SEQ ID NO: 1 as a ligand, and 50 μL of a sample solution diluted to 25 μM with an acetate buffer of pH 4.0 was used in place of 500 μL of a sample solution diluted to 100 μM with a HEPES buffer.

(2) Using the thus-prepared immobilized carrier V and in the same manner as in Example 1, antibody binding properties, selectivity, alkali resistance, and temporal stability were evaluated. The evaluation results are shown in the corresponding column of Table 2.

Further, the dissociation rate Koff was $1.5 \times 10^{-4}$ [1/s].

Example 23

(1) An "immobilized carrier W" was prepared in the same manner as in Example 1, except that a polypeptide having a primary structure shown in the column "Ligand" of Example 23 in Table 2 was used in place of a polypeptide as set forth in SEQ ID NO: 1 as a ligand, and 50 μL of a sample solution diluted to 25 μM with an acetate buffer of pH 4.0 was used in place of 500 μL of a sample solution diluted to 100 μM with a HEPES buffer.

(2) Using the thus-prepared immobilized carrier W and in the same manner as in Example 1, antibody binding properties, selectivity, alkali resistance, and temporal stability were evaluated. The evaluation results are shown in the corresponding column of Table 2.

Further, the dissociation rate Koff was $1.6 \times 10^{-4}$ [1/s].

Example 24

(1) An "immobilized carrier" was prepared in the same manner as in Example 1, except that a polypeptide having a primary structure shown in the column "Ligand" of Example 24 in Table 2 was used in place of a polypeptide as set forth in SEQ ID NO: 1 as a ligand.

(2) Using the thus-prepared immobilized carrier W and in the same manner as in Example 1, antibody binding properties, selectivity, alkali resistance, and temporal stability were evaluated. The evaluation results are shown in the corresponding column of Table 2.

Further, the dissociation rate Koff was $1.3 \times 10^{-4}$ [1/s].

Example 25

(1) An "immobilized carrier Y" was prepared in the same manner as in Example 1, except that a fusion polypeptide having a primary structure shown in the column "Ligand" of Example 25 in Table 2 was used in place of a polypeptide as set forth in SEQ ID NO: 1 as a ligand.

(2) Using the thus-prepared immobilized carrier Y and in the same manner as in Example 1, antibody binding properties, selectivity, alkali resistance, and temporal stability were evaluated. The evaluation results are shown in the corresponding column of Table 2.

Further, the dissociation rate Koff was $1.9 \times 10^{-4}$ [1/s].

Comparative Example 1

(1) An "immobilized carrier Z" was prepared in the same manner as in Example 1, except that a wild-type protein A (manufactured by Repligen Corporation) was used in place of a polypeptide as set forth in SEQ ID NO: 1 as a ligand, and 10 μL of a sample solution diluted to 50 nM with an acetate buffer of pH 5.0 was used in place of 500 μL of a sample solution diluted to 100 μM with a HEPES buffer.

(2) Using the thus-prepared immobilized carrier Z and in the same manner as in Example 1, antibody binding properties, selectivity, alkali resistance, and temporal stability were evaluated. The evaluation results are shown in the corresponding column of Table 2.

Further, the dissociation rate Koff was $2.5 \times 10^{-4}$ [1/S].

Comparative Example 2

(1) An "immobilized carrier AA" was prepared in the same manner as in Example 1, except that a modified protein A (manufactured by Sino Biological Inc.) was used in place of a polypeptide as set forth in SEQ ID NO: 1 as a ligand, and 10 μof a sample solution diluted to 100 nM with an acetate buffer of pH 5.0 was used in place of 500 μL of a sample solution diluted to 100 μM with a HEPES buffer.

(2) Using the thus-prepared immobilized carrier AA and in the same manner as in Example 1, antibody binding properties, selectivity, alkali resistance, and temporal stability were evaluated. The evaluation results are shown in the corresponding column of Table 2.

Further, the dissociation rate Koff was $3.2 \times 10^{-4}$ [1/s].

Comparative Example 3

(1) An "immobilized carrier AB" was prepared in the same manner as in Example 1, except that a low molecular weight compound ApA (the following chemical formula) synthesized according to the synthesis method described in Li, R., Dowd, V., Steward, D. J., Burton, S. J., and Lowe, C. R., 1998, Nature Biotechnology, Vol. 16, pp. 190 to 195 was used in place of a polypeptide as set forth in SEQ ID NO: 1 as a ligand.

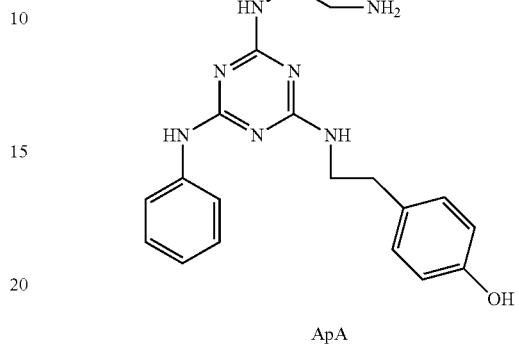

ApA (2) Using the thus-prepared immobilized carrier AB and in the same manner as in Example 1, antibody binding properties, selectivity, alkali resistance, and temporal stability were evaluated. The evaluation results are shown in the corresponding column of Table 2.

Further, the dissociation rate Koff was $6.5 \times 10^{-4}$ [1/s].

Comparative Example 4

(1) An "immobilized carrier AC" was prepared in the same manner as in Example 1, except that a polypeptide as set forth in SEQ ID NO: 26 was used in place of a polypeptide as set forth in SEQ ID NO: 1 as a ligand.

(2) Using the thus-prepared immobilized carrier AC and in the same manner as in Example 1, antibody binding properties, selectivity, alkali resistance, and temporal stability were evaluated. The evaluation results are shown in the corresponding column of Table 2.

Further, the dissociation rate Koff was $2.4 \times 10^{-4}$ [1/s].

TABLE 2

| | | Ligand | | | Immobilized carrier | | | | |
|---|---|---|---|---|---|---|---|---|---|
| | | Primary structure (N-terminal→ C-terminal) or name | Number of amino acid residues | SEQ ID NO. | Symbol | Antibody binding properties | Selectivity | Alkali resistance | Temporal stability |
| Examples | 1 | EQQNAFY | 7 | 1 | A | A | A | A | A |
| | 2 | KEQQNAFY | 8 | 2 | B | A | A | A | A |
| | 3 | EQQNAFYEILH | 11 | 3 | C | A | A | A | A |
| | 4 | EQQNAFYEILHL | 12 | 4 | D | A | A | A | A |
| | 5 | EGQNAFY | 7 | 5 | E | A | A | A | A |
| | 6 | KKKEQQNAFYKKK | 13 | 6 | F | A | A | A | A |
| | 7 | KKKEQQNAFYEILHKKK | 17 | 7 | G | A | A | A | A |
| | 8 | EQQNAFYGGGKGGGEQQNAFY | 21 | 8 | H | A | A | A | A |
| | 9 | EQNAFY | 6 | 9 | I | A | A | A | A |
| | 10 | EQQSAFY | 7 | 10 | J | A | A | A | A |
| | 11 | EQQSAFYEILH | 11 | 11 | K | A | A | A | A |
| | 12 | DQQSAFY | 7 | 12 | L | A | A | A | A |
| | 13 | DQQSAFYEILH | 11 | 13 | M | A | A | A | A |
| | 14 | EAQQSAFY | 8 | 14 | N | A | A | A | A |
| | 15 | EQSAFY | 6 | 15 | O | A | A | A | A |
| | 16 | EAQQNAFY | 7 | 16 | P | A | A | A | A |
| | 17 | DAQQSAFY | 8 | 17 | Q | A | A | A | A |

TABLE 2-continued

|  |  | Ligand | | | Immobilized carrier | | | | |
|---|---|---|---|---|---|---|---|---|---|
|  |  | Primary structure (N-terminal→ C-terminal) or name | Number of amino acid residues | SEQ ID NO. | Symbol | Antibody binding properties | Selectivity | Alkali resistance | Temporal stability |
|  | 18 | DQSAFY | 6 | 18 | R | A | A | A | A |
|  | 19 | EQQNAFY-NH$_2$ | 7 | 19 | S | A | A | A | A |
|  | 20 | Ac-EQQNAFYK | 8 | 20 | T | A | A | A | A |
|  | 21 | Ac-EQQNAFYEILHK | 12 | 21 | U | A | A | A | A |
|  | 22 | Ac-KKKEQQNAFYKKK | 13 | 22 | V | A | A | A | A |
|  | 23 | Ac-KKKEQQNAFYEILHKKK | 17 | 23 | W | A | A | A | A |
|  | 24 | H$_2$N-(peg)$_8$-EQQNAFYE | 8 | 24 | X | A | A | A | A |
|  | 25 | Ac-EQQNAFY-(peg)$_8$-K-(peg)$_8$-EQQNAFY | 15 | 25 | Y | A | A | A | A |
| Comparative Examples | 1 | Wild type protein A/SpA | — | — | Z | A | A | D | D |
|  | 2 | Modified protein A | — | — | AA | A | A | D | D |
|  | 3 | Low molecular weight compound ApA | — | — | AB | E | D | A | A |
|  | 4 | QQNAFYEI | 8 | 26 | AC | C | D | A | A |

From the foregoing results, it was demonstrated that all the antibody-binding polypeptides of Examples 1 to 25 have antibody binding properties and selectivity comparable to those of native protein A, and exhibit superior alkali resistance and temporal stability as compared with native protein A and modified protein A.

Further, since both native protein A and modified protein A have antigenicity whereas the antibody-binding polypeptide of the present invention does not have antigenicity, it is highly safe to the human body even when the antibody-binding polypeptide of the present invention is incorporated into purified antibodies in a case of being used as a ligand for affinity chromatographic purification.

Further, when comparing the antibody-binding polypeptides of Examples 1 to 25 with the polypeptide (QQNAFYEI)(SEQ ID NO: 26) of Comparative Example 4, the polypeptide of Comparative Example 4 exhibits poor antibody binding properties and selectivity, thus failing to reach the required level.

INDUSTRIAL APPLICABILITY

The antibody-binding polypeptide and adsorption material of the present invention are useful as a purification member for antibody drugs. Further, the antibody-binding polypeptide of the present invention is also useful as a linker for labeling an antibody, or a linker for an antibody drug conjugate.

SEQUENCE LISTING

International Application No. W-5420PCT ANTIBODY-BINDING POLYPEPTIDE, ANTIBODY-BINDING based on international receipt under the patent cooperation treaty
JP15075157  20150904—000500044951501773276  normal
20150904091646201508251433374700_P1AP101_W-_4.app

What is claimed is:

1. An antibody-binding polypeptide having a sequence homology of 85% or more to a polypeptide as set forth in any one of SEQ ID NOs: 6-9 and 15-18.

2. The antibody-binding polypeptide according to claim 1, wherein 1 to 24 ethylene glycol units are covalently bound to at least one place selected from the N-terminal, the C-terminal, and the amino acid residue side chain of the antibody-binding polypeptide.

3. The antibody-binding polypeptide according to claim 1, wherein at least one place selected from the N-terminal, the C-terminal, and the amino acid residue side chain of the antibody-binding polypeptide is modified.

4. An antibody-binding polypeptide having a sequence as set forth in any one of SEQ ID NOs: 6-9 and 15-18.

5. The antibody-binding polypeptide according to claim 4, wherein 1 to 24 ethylene glycol units are covalently bound to at least one place selected from the N-terminal, or the C-terminal, of the antibody-binding polypeptide.

6. The antibody-binding polypeptide according to claim 4, wherein at least one place selected from the N-terminal, or the C-terminal, of the antibody-binding polypeptide is modified.

7. An antibody-binding fusion polypeptide in which 2 to 10 domain units are fused by a covalent bond, taking an antibody-binding polypeptide having a sequence as set forth in any one of SEQ ID NOs: 6-9 and 15-18 as one domain unit,
wherein the antibody-binding fusion polypeptide further comprises a linker connecting between the foregoing domain units, and
wherein the linker is at least one linker selected from the group consisting of a PEG linker consisting of 1 to 24 ethylene glycol units per one linker.

8. The antibody-binding fusion polypeptide according to claim 7, wherein 1 to 24 ethylene glycol units are covalently bound to at least one place selected from the N-terminal, or the C-terminal, of the antibody-binding fusion polypeptide.

9. The antibody-binding fusion polypeptide according to claim 7, wherein at least one place selected from the N-terminal, or the C-terminal, of the antibody-binding fusion polypeptide is modified.

10. The antibody-binding fusion polypeptide according to claim 7, wherein the total molecular weight of amino acid residues contained in the domain unit and amino acid residues contained in the linker is 5000 or less.

11. An adsorption material of an antibody or an antibody derivative, in which an antibody-binding polypeptide having a sequence homology of 85% or more to a polypeptide as set forth in any one of SEQ ID NOs: 6-9 and 15-18, an antibody-binding polypeptide as set forth in any one of SEQ ID NOs: 6-9 and 15-18, or an antibody-binding fusion polypeptide in which 2 to 10 domain units are fused by a covalent bond, taking an antibody-binding polypeptide as set forth in any one of SEQ ID NOs: 6-9 and 15-18 as one domain unit is immobilized on a water-insoluble carrier,
wherein the antibody-binding fusion polypeptide further comprises a linker connecting between the foregoing domain units, and
wherein the linker is at least one linker selected from the group consisting of a PEG linker consisting of 1 to 24 ethylene glycol units per one linker.

* * * * *